United States Patent
Hammerschmidt et al.

(10) Patent No.: US 12,414,989 B2
(45) Date of Patent: Sep. 16, 2025

(54) MEANS AND METHODS FOR TREATING HERPESVIRUS INFECTION

(71) Applicant: HELMHOLTZ ZENTRUM MÜNCHEN-DEUTSCHES FORSCHUNGSZENTRUM FÜR GESUNDHEIT UND UMWELT (GMBH), Neuherberg (DE)

(72) Inventors: Wolfgang Hammerschmidt, Munich (DE); Reinhard Zeidler, Olching (DE); Dagmar Pich, Munich (DE)

(73) Assignee: Helmholtz Zentrum München Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 0 days.

(21) Appl. No.: 18/182,212

(22) Filed: Mar. 10, 2023

(65) Prior Publication Data

US 2023/0277656 A1    Sep. 7, 2023

Related U.S. Application Data

(63) Continuation of application No. 16/080,292, filed as application No. PCT/EP2017/054615 on Feb. 28, 2017, now Pat. No. 11,602,560.

(30) Foreign Application Priority Data

Mar. 1, 2016  (EP) .................................. 16000493
Mar. 17, 2016 (LU) .......................................... 93002

(51) Int. Cl.
    A61K 39/245    (2006.01)
    A61K 39/00     (2006.01)
    A61P 31/22     (2006.01)
    C12N 7/00      (2006.01)

(52) U.S. Cl.
    CPC ............ *A61K 39/245* (2013.01); *A61P 31/22* (2018.01); *C12N 7/00* (2013.01); *A61K 2039/5258* (2013.01); *A61K 2039/53* (2013.01); *C12N 2710/16223* (2013.01); *C12N 2710/16234* (2013.01); *C12N 2710/16252* (2013.01); *C12N 2710/16623* (2013.01); *C12N 2710/16634* (2013.01); *C12N 2710/16652* (2013.01)

(58) Field of Classification Search
    CPC .......... A61K 39/245; A61K 2039/5258; A61K 2039/53; A61P 31/22; C12N 7/00; C12N 2710/16223; C12N 2710/16234; C12N 2710/16252; C12N 2710/16623; C12N 2710/16634; C12N 2710/16652; C12N 2710/16034; C12N 2710/16023
    See application file for complete search history.

(56) References Cited

U.S. PATENT DOCUMENTS

| | | | |
|---|---|---|---|
| 9,517,261 B2* | 12/2016 | Feederle | A61K 39/245 |
| 10,300,129 B2 | 5/2019 | Ruiss et al. | |
| 11,602,560 B2 | 3/2023 | Hammerschmidt et al. | |
| 2014/0227305 A1* | 8/2014 | Lange-Ruiss | A61K 39/12 435/69.3 |
| 2014/0322255 A1 | 10/2014 | Feederle et al. | |
| 2019/0282691 A1* | 9/2019 | Delecluse | A61P 43/00 |
| 2021/0196815 A1 | 7/2021 | Hammerschmidt et al. | |

FOREIGN PATENT DOCUMENTS

| | | |
|---|---|---|
| JP | 2013541507 A | 11/2013 |
| JP | 2015503915 A | 2/2015 |
| WO | WO-2012025603 A1 | 3/2012 |
| WO | WO-2013098364 A1 | 7/2013 |

OTHER PUBLICATIONS

Bergallo M, Merlino C, Montin D, Galliano I, Gambarino S, Mareschi K, Fagioli F, Montanari P, Martino S, Tovo PA. Development of a Low-Cost Stem-Loop Real-Time Quantification PCR Technique for EBV miRNA Expression Analysis. Mol Biotechnol. Sep. 2016; 58(8-9):540-50. (Year: 2016).*

Wang Y, Guo Z, Shu Y, Zhou H, Wang H, Zhang W. Bart miRNAs: an unimaginable force in the development of nasopharyngeal carcinoma. Eur J Cancer Prev. Mar. 2017;26(2):144-150. (Year: 2017).*

Shumilov A, Tsai MH, Schlosser YT, Kratz AS, Bernhardt K, Fink S, Mizani T, Lin X, Jauch A, Mautner J, Kopp-Schneider A, Feederle R, Hoffmann I, Delecluse HJ. Epstein-Barr virus particles induce centrosome amplification and chromosomal instability. Nat Commun. Feb. 10, 2017;8:14257. (Year: 2017).*

Kang D, Skalsky RL, Cullen BR. EBV BART MicroRNAs Target Multiple Pro-apoptotic Cellular Genes to Promote Epithelial Cell Survival. PLoS Pathog. Jun. 12, 2015;11(6):e1004979. doi: 10.1371/journal.ppat. 1004979. PMID: 26070070; PMCID: PMC4466530. (Year: 2015).*

Pavlova S, Feederle R, Gärtner K, Fuchs W, Granzow H, Delecluse HJ. An Epstein-Barr virus mutant produces immunogenic defective particles devoid of viral DNA. J Virol. Feb. 2013;87(4):2011-22. Epub Dec. 12, 2012. (Year: 2012).*

Miller G, Heston L, Countryman J. P3HR-1 Epstein-Barr virus with heterogeneous DNA is an independent replicon maintained by cell-to-cell spread. J Virol. Apr. 1985;54(1):45-52. (Year: 1985).*

Ikuta K, Srinivas SK, Schacker T, Miyagi J, Scott RS, Sixbey JW. Points of recombination in Epstein-Barr virus (EBV) strain P3HR-1-derived heterogeneous DNA as indexes to EBV DNA recombinogenic events in vivo. J Virol. Dec. 2008;82(23):11516-25. Epub Sep. 25, 2008. (Year: 2008).*

(Continued)

*Primary Examiner* — Rachel B Gill

(57) ABSTRACT

The present invention provides herpesviruses, such as EBV, which lack at least one viral miRNA. Such herpesviruses lacking at least one viral miRNA are advantageously not capable of packaging their genome into the capsid, thereby producing HVLPs, which are substantially free of their herpesvirus genome or the nucleic acid molecule encoding the proteinaceous part of the HVLP and viral miRNA. Such HVLPs may be used as vaccine.

19 Claims, 19 Drawing Sheets

Figure 1:
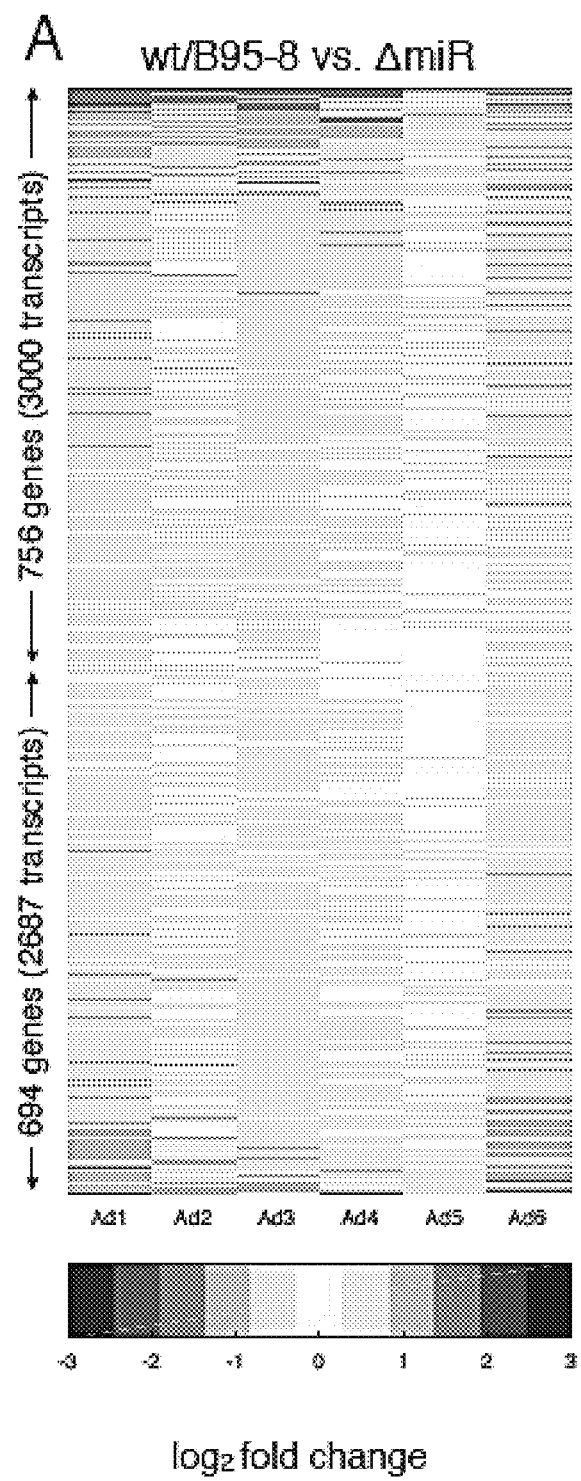
Figure 1:
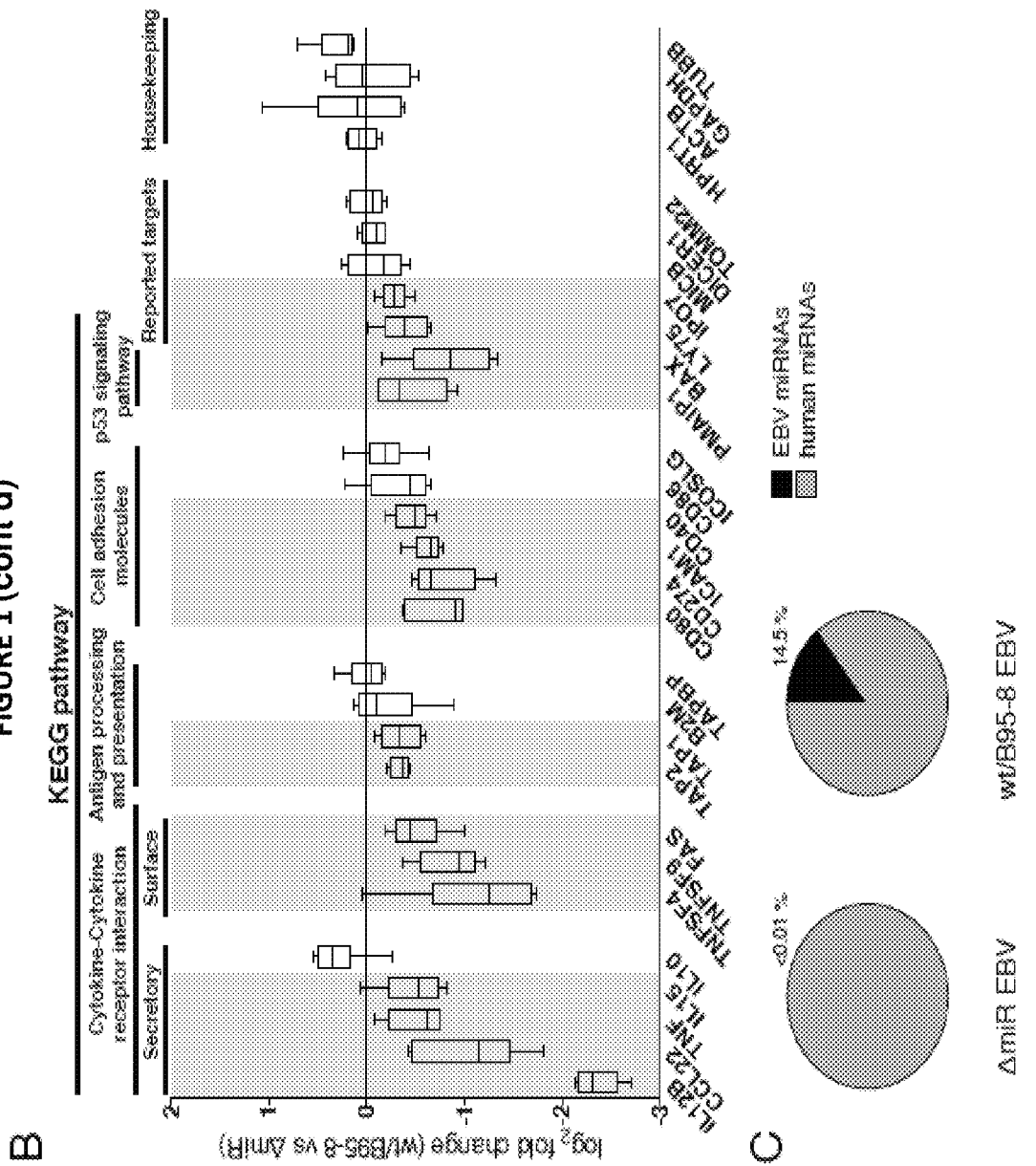

Specification includes a Sequence Listing.

(56) References Cited

OTHER PUBLICATIONS

Heilingloh, et al., "Role of L-Particles during Herpes Simplex Virus Infection," Front Microbiol, Dec. 19, 2017, 7 pages.
Hettich et al., "Genetic design of an optimized packaging cell line for gene vectors transducing human B cells," Gene Therapy, 2006, pp. 844-856.
Jochum et al., "RNAs in Epstein-Barr virions control early steps of infection," Proc Natl Acad Sci., May 22, 2012, pp. E1396-E1404.
Kimura, et al., "Deletion of Viral microRNAs in the Oncogenesis of Epstein-Barr Virus-Associated Lymphoma," Front Microbial., Jul. 8, 2021, 7 pages.
Seto et al., Micro RNAs of Epstein-Barr virus promote cell cycle progression and prevent apoptosis of primary human B cells, PLoS Pathog., Aug. 2010, 16 pages.
Skalsky, et al., EBV Noncoding RNAs, Curr Top Microbiol Immunuol., 2015, pp. 181-217.
Barth S., et al., "Epstein-Barr Virus-Encoded MicroRNA miR-BART2 Down-Regulates the Viral DNA Polymerase BALF5," Nucleic Acids Res, 2008, vol. 36(2), pp. 666-675.
Johannsen E., et al., "Proteins of Purified Epstein-Barr Virus," Proc Natl Acad Sci U S A, 2004, vol. 101(46), pp. 16286-16291.
Poling B. C., et al., "The Epstein-Barr Virus miR-BHRF1 MicroRNAs Regulate Viral Gene Expression in cis," Virology, 2017, vol. 512, pp. 113-123.
Raymondwai-Ming Lung., "Modulation of LMP2A Expression by a Newly Identified Epstein-Barr Virus-Encoded MicroRNA miR-BART22," Neoplasia, 2009, vol. 11(11), pp. 1174-1184.
Riley K. J., et al., "EBV and Human MicroRNAs Co-Target Oncogenic and Apoptotic Viral and Human Genes During Latency," The EMBO Journal, 2012, vol. 31(9), pp. 2207-2221.
Adhikary, et al., "Control of Epstein-Barr virus infection in vitro by T helper cells specific for virion glycoproteins," J Exp Med. Apr. 17, 2006; 203(4):995-1006. Epub Mar. 20, 2006.
Adhikary, et al., "Immunodominance of lytic cycle antigens in Epstein-Barr virus-specific CD4+ T cell preparations for therapy," PLoS One. Jul. 4, 2007; 2(7):e583.
Altschul, et al., "Gapped BLAST and PSI-BLAST: a new generation of protein database search programs," Nucleic Acids Res. Sep. 1, 1997; 25(17):3389-402.
Author Unknown, World Health Organization International Agency for Research on Cancer, IARC Working Group, IARC Monographs on the Evaluation of Carcinogenic Risks to Humans, Jun. 14-21, 2006, Lyon, France, vol. 94 Ingested Nitrate and Nitrite, and Cyanobacterial Peptide Toxins, 2010, 464 pages.
Balfour, Jr., H.H., "Progress, prospects, and problems in Epstein-Barr virus vaccine development," Curr Opin Virol. Jun. 2014; 6:1-5. Epub Mar. 15, 2014.
Bartel, D.P., "MicroRNAs: target recognition and regulatory functions," Cell. Jan. 23, 2009; 136(2):215-33.
Boss, et al., "Role of virus-encoded microRNAs in herpesvirus biology," Trends Microbiol. Dec. 2009; 17(12):544-53. Epub Oct. 12, 2009.
Cohen, et al., "Epstein-Barr virus: an important vaccine target for cancer prevention," Sci Transl Med. Nov. 2, 2011; 3(107):107fs7, 3 pages.
Cohen, et al., "The need and challenges for development of an Epstein-Barr virus vaccine," Vaccine. Apr. 18, 2013; 31 Suppl 2(0 2):B194-6, 3 pages.
Delecluse, et al., "A first-generation packaging cell line for Epstein-Barr virus-derived vectors," Proc Natl Acad Sci USA. Apr. 27, 1999; 96(9):5188-93.
Dölken, et al., "Systematic analysis of viral and cellular microRNA targets in cells latently infected with human gamma-herpesviruses by RISC immunoprecipitation assay," Cell Host and Microbe, 2010, 7(4), pp. 324-334.

Ensembl Transcript ENST00000231228.3, 5 pages retrieved online on Mar. 1, 2025 at: https://www.genome-euro.ucsc.edu/cgi-bin/hgGene?org=Human&hgg_gene=uc003lxr.2&hgg_chrom=none&db=hg38.
Ensembl Transcript ENST00000374897.4, 1 page retrieved online on Mar. 1, 2025 at: www.ensembl.org/Homo_sapiens/Transcript/Summary?g=ENSG00000204267;r=6:32825415-32838739;t=ENST00000374897.
Genbank Accession No. AJ507799.2, version 2 as of Jul. 26, 2016, 70 pages retrieved online on Mar. 1, 2025 at: https://www.ncbi.nlm.nih.gov/nuccore/AJ507799.
Genbank Accession No. NC_009334.1, version 1 as of Aug. 13, 2018, 58 pages retrieved online on Mar. 1, 2025 at: https://www.ncbi.nlm.nih.gov/nuccore/NC_009334.1.
Genbank Accession No. V01555.2, version 2 as of Jul. 26, 2016, 68 pages retrieved online on Mar. 1, 2025 at: https://www.ncbi.nlm.nih.gov/nuccore/V01555.
Genbank Accession No. NC_007605.1, version 1 as of Aug. 13, 2018, 78 pages retrieved online on Mar. 1, 2025 at: https://www.ncbi.nlm.nih.gov/nuccore/NC_007605.1.
Horst, et al., "Specific targeting of the EBV lytic phase protein BNLF2a to the transporter associated with antigen processing results in impairment of HLA class I-restricted antigen presentation," J Immunol. Feb. 15, 2009; 182(4):2313-24.
Iskra, et al., "Toll-like receptor agonists synergistically increase proliferation and activation of B cells by Epstein-Barr virus," J Virol. Apr. 2010; 84(7):3612-23. Epub Jan. 20, 2010.
Kalla, et al., "AP-1 homolog BZLF1 of Epstein-Barr virus has two essential functions dependent on the epigenetic state of the viral genome," Proc Natl Acad Sci USA. Jan. 12, 2010; 107(2):850-5. Epub Dec. 22, 2009.
Kieff, E., et al., "Epstein-Barr virus and its replication," In: Field's Virology, 2007, Lippincott Williams & Wilkins, Philadelphia, pp. 2603-2654.
Kuzembayeva, et al., "Comparing proteomics and RISC immunoprecipitations to identify targets of Epstein-Barr viral miRNAs," PLoS One. 2012; 7(10):e47409, 9 pages. Epub Oct. 16, 2012.
Lautscham, et al., "Processing of a multiple membrane spanning Epstein-Barr virus protein for CD8(+) T cell recognition reveals a proteasome-dependent, transporter associated with antigen processing-independent pathway," J Exp Med. Oct. 15, 2001; 194(8):1053-68.
Mynarek, et al., "Posttransplant lymphoproliferative disease after pediatric solid organ transplantation," Clin Dev Immunol. 2013; 2013:814973, 14 pages. Epub Sep. 24, 2013.
Nachmani, et al., "Diverse herpesvirus microRNAs target the stress-induced immune ligand MICB to escape recognition by natural killer cells," Cell Host Microbe. Apr. 23, 2009; 5(4):376-85.
Rees, et al., "A phase I trial of epstein-barr virus gp350 vaccine for children with chronic kidney disease awaiting transplantation," Transplantation. Oct. 27, 2009; 88(8):1025-9.
Ruiss, et al., "A virus-like particle-based Epstein-Barr virus vaccine," J Virol. Dec. 2011; 85(24):13105-13. Epub Oct. 12, 2011.
Skalsky, et al., "The viral and cellular microRNA targetome in lymphoblastoid cell lines," PLoS Pathog. Jan. 2012; 8(1):e1002484, 19 pages. Epub Jan. 26, 2012.
Sokal, et al., "Recombinant gp350 vaccine for infectious mononucleosis: a phase 2, randomized, double-blind, placebo-controlled trial to evaluate the safety, immunogenicity, and efficacy of an Epstein-Barr virus vaccine in healthy young adults," J Infect Dis. Dec. 15, 2007; 196(12):1749-53.
Szabo, et al., "Molecular mechanisms regulating Th1 immune responses," Annu Rev Immunol. 2003; 21:713-58. Epub Dec. 19, 2001.
Thorley-Lawson, D.A., "EBV the prototypical human tumor virus—just how bad is it?," J Allergy Clin Immunol. Aug. 2005; 116(2):251-61.

\* cited by examiner

Figure 2:
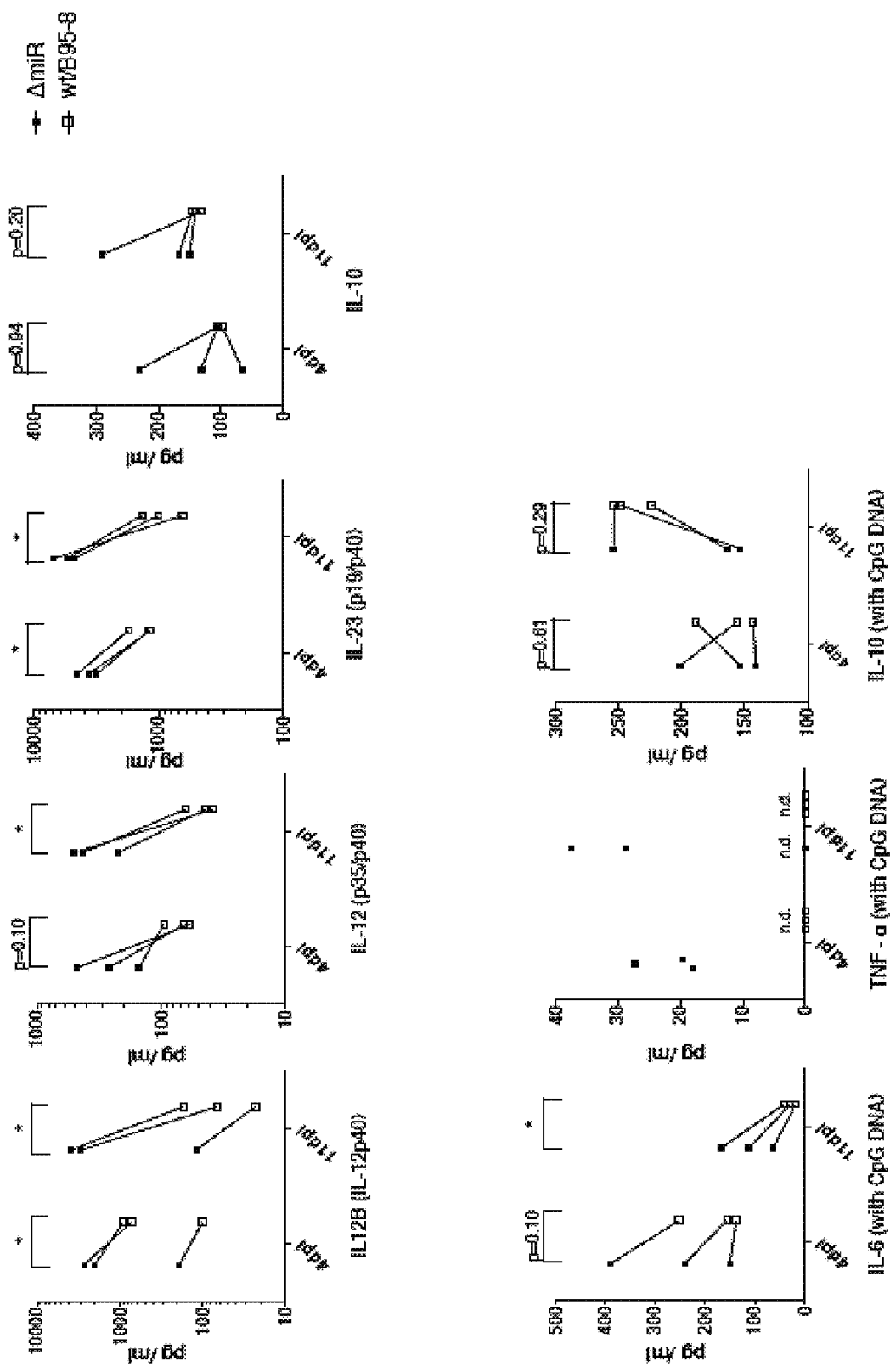
Figure 2:
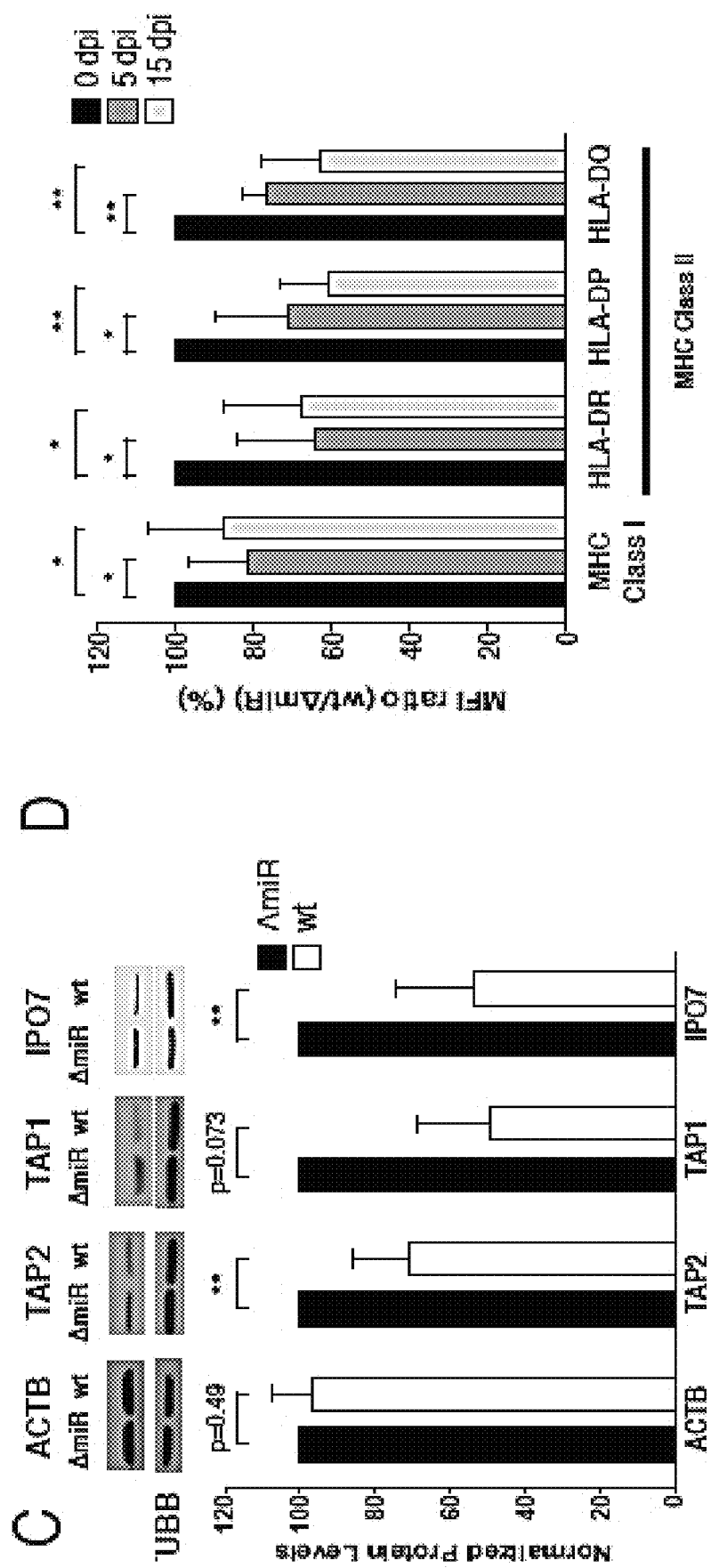

FIGURE 2 (cont'd)
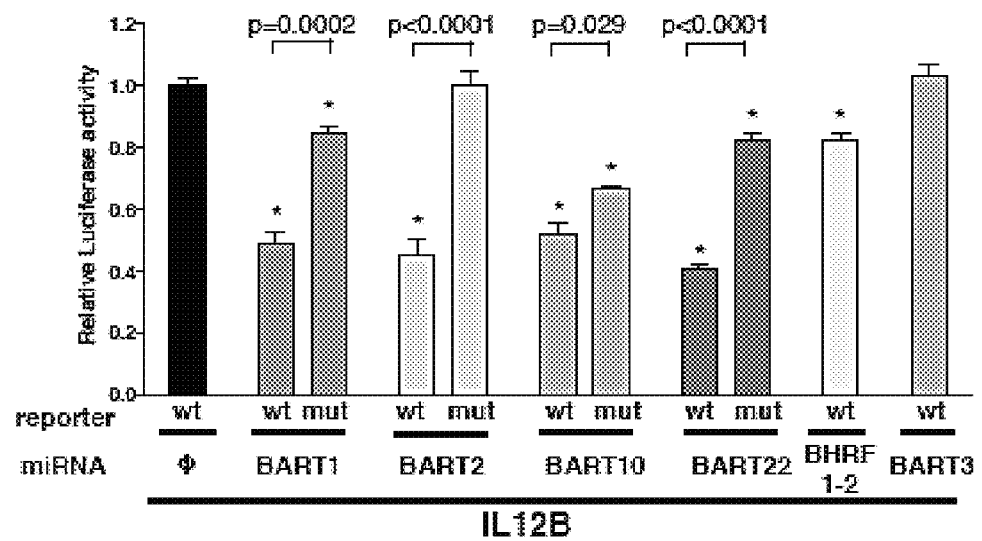
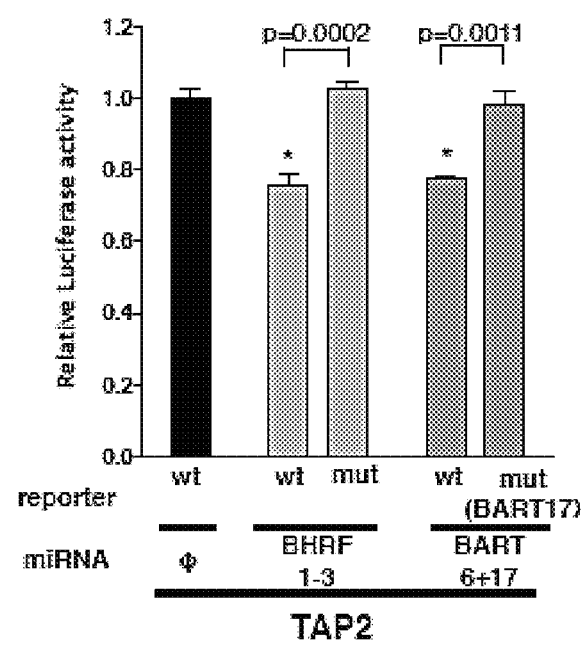

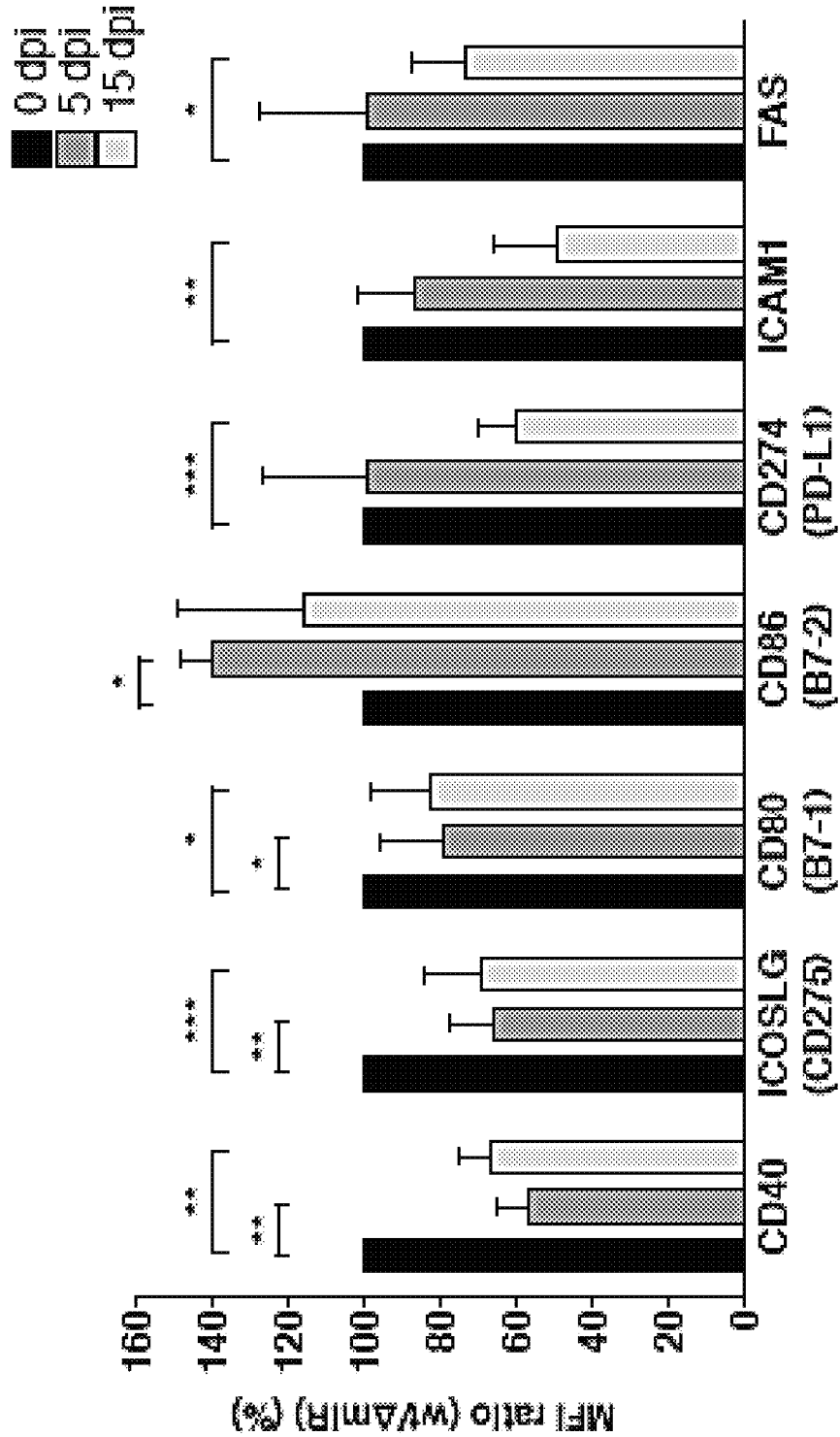

Figure 3:
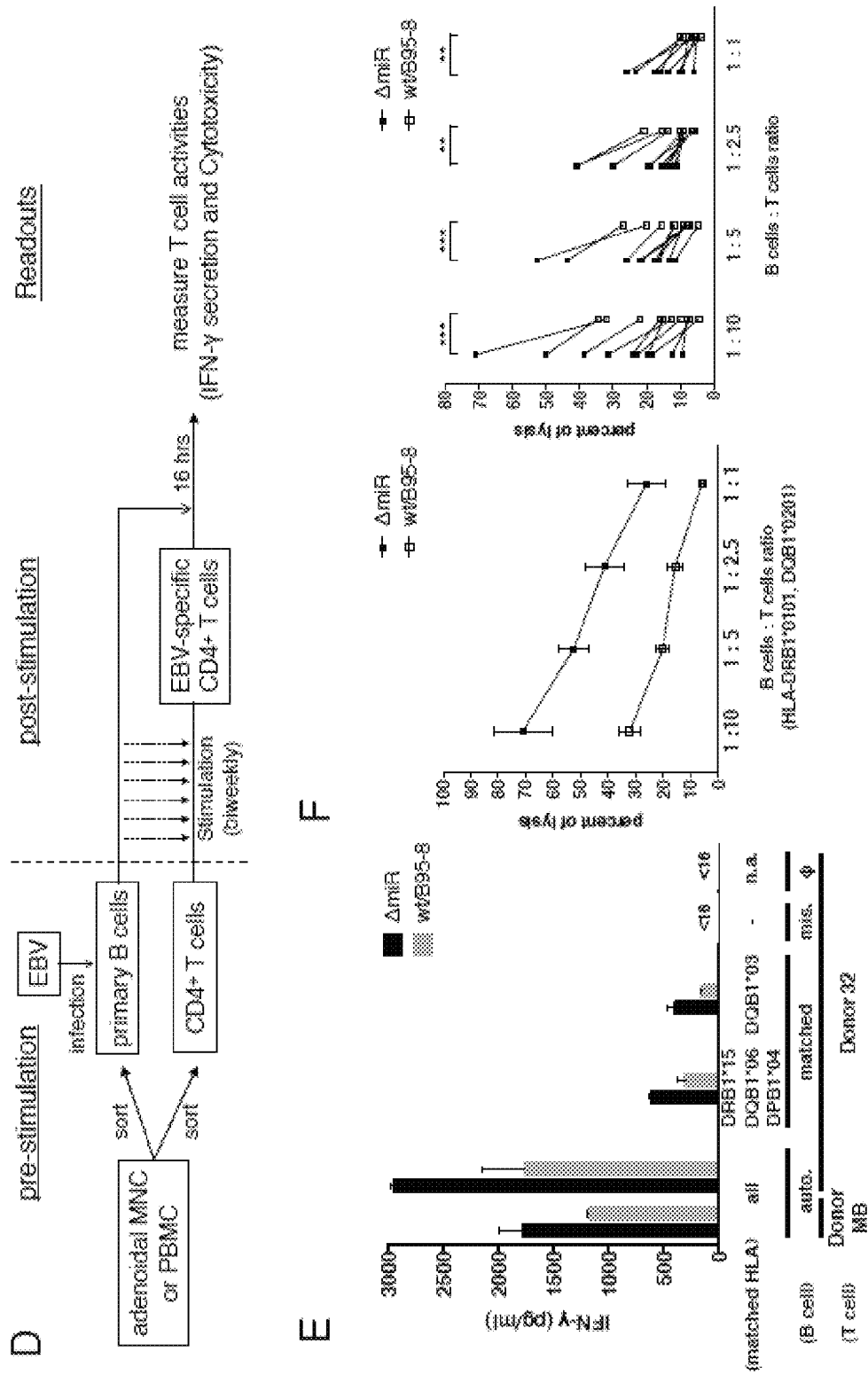

FIGURE 3
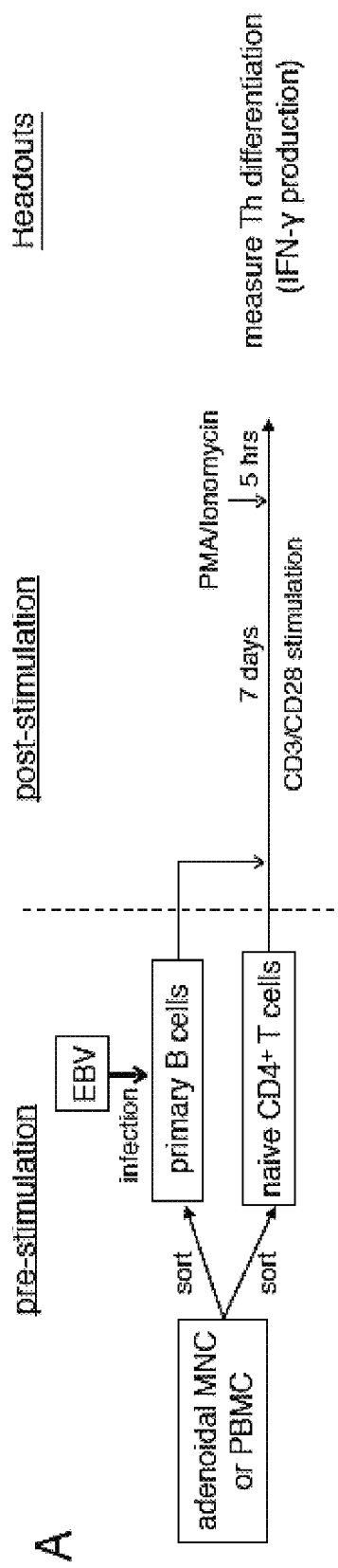
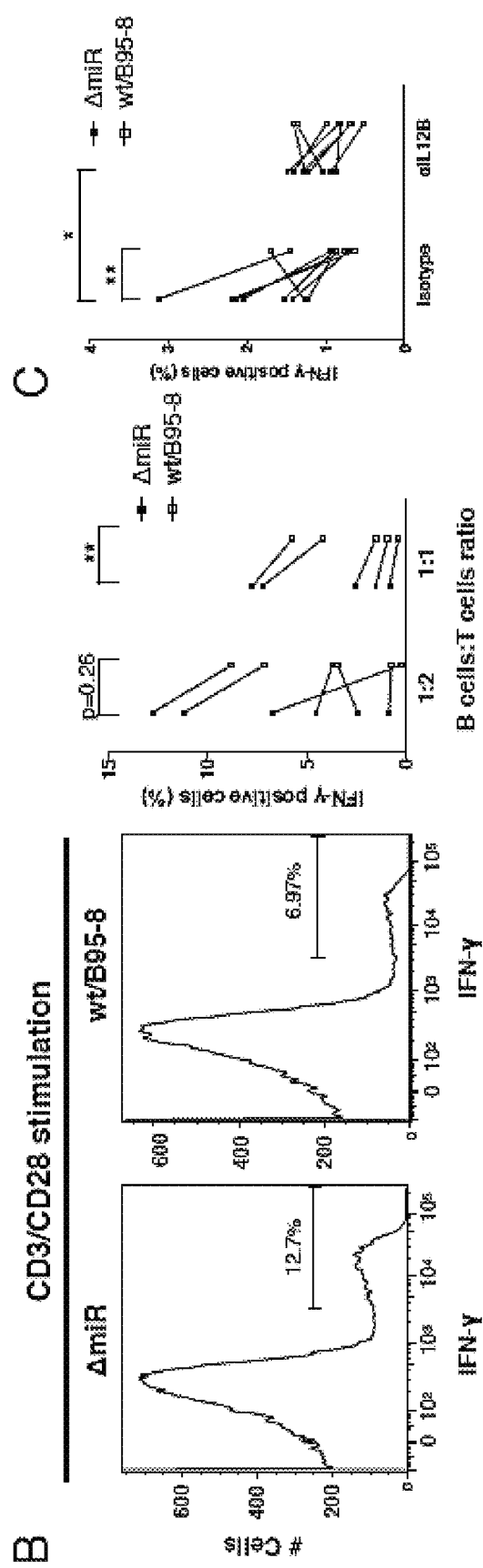

Figure 7

*IL12B mut (BART2)*

```
target  5'  GGCAGGUGGCUUCUUAACAGCCCUGUGAGAAGCAGACAGAUGCAAAGAAAAUC  3'
              |||:| |||                |        :|||||  ||||||
miRNA   3'  CGUUC CCG                 C        UUACGU  CUUUUAU  5'
              |||:| |||                |        :|||||  |XXXX|
mut     5'  GGCAGGUGGCUUCUUAACAGCCCUGUGAGAAGCAGACAGAUGCAAAGUUUUUC  3' target  5'  AGCAUGUUUGAACCUGAUACACAAUUAUGACCAGAAAAUAU  3'
              ||| | :||              |||  |||||||||
miRNA   3'  CGUUCCCGCU              UAC  GUCUUUUAU  5'
              ||| | :||              |||  |||XXXX||
mut     5'  AGCAUGUUUGAACCUGAUACACAAUUAUGACCAGUUUUUAU  3'
```

*IL12B mut (BART10)*

```
target  5'  UCAGCUAAU       UUAUGUAU  3'
              ||||:|||       ||||||||
miRNA   3'  UGUCGGUUGAGGUACCAAUACAU  5'
              ||||:|||       ||XXXX|
mut     5'  UCAGCUAAU       UUUACAAU  3' target  5'  GGGCCUUCAUGCUAUUUAAAUAUUUAAGUAAUUUAUGUAU  3'
              :||| |  |:||         |        |||||||
miRNA   3'  UGUCGGUUGA  GGUA           CC    AAUACAU  5'
              :||| |  |:||         |        ||XXXX|
mut     5'  GGGCCUUCAUGCUAUUUAAAUAUUUAAGUAAUUUUACAAU  3'
```

*IL12B mut (BART22)*                                *TAP2 mut (BHRF1-3)*

```
target  5'   GGCUGAACUAAUAAAAACUCUUCUUUGUAAU  3'    target  5'   GUCCCGUUGU  3'
               :||| ||:|            ||||||||                    ||||||||
miRNA   3'   UGAUGAUCUGGUACU    GAAACAUU  5'        miRNA   3'  ACACGAAUGUGUGAAGGGCAAU  5'
               :||| ||:|            ||XXXX||                              |||XXXX|
mut     5'   GGCUGAACUAAUAAAAACUCUUCUAACAAAU  3'    mut     5'   GUCCGCAAGU  3'
```

*IL12B mut (BART1)*                                 *TAP2 mut (BART17)*

```
target  5'  AAUAUGGCUCCAUGAAGGUGCUAC  3'          target  5'   GGUUUGCUAAUUCCUCUUGC  3'
              |:||:|||| ||: |||||||                              |::|||    ||||||||:
miRNA   3'  CUGUAUCACC UAUCGCCACGAU  5'           miRNA   3'  GAACAUACGGACGC   AGGAGAAU  5'
              |:||:|||| ||: |XXXX||                              |::|||    ||XXXX|:
mut     5'  AAUAUGGCUCCAUGAAGCACGUAC  3'          mut     5'   GGUUUGCUAAUUCGAGAUGC  3' target  5'      UCCUACUAUCCUCUUU  3'
                                                                    |||  |||||||
                                                   miRNA   3'  GAACAUACGGACGC AGGAGAAU  5'
                                                                    |||  ||XXXX|
                                                   mut     5'      UCCUACUAUCGAGAUU  3'
```

Figure 11
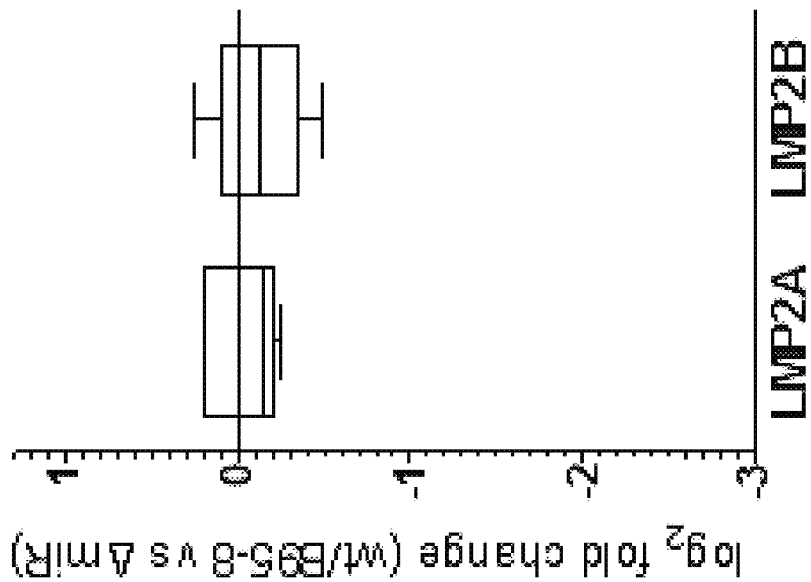
b
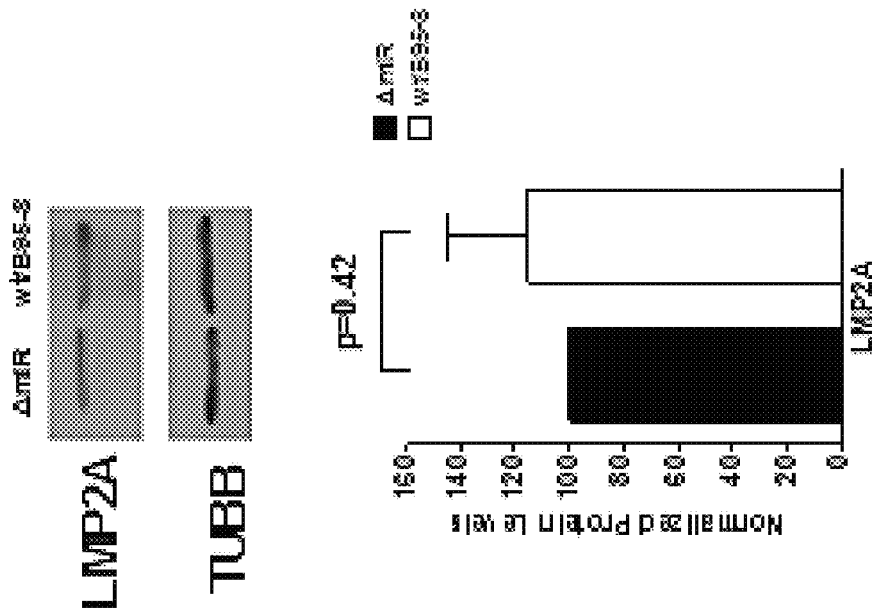

Figure 12

| Donor | HLA class I | HLA class II |
|---|---|---|
| MB | n.a. | DRB1*0301, *0701; |
| JM | n.a. | DRB1*0801, *1301; DQB1*0402, *0603; DPB1*0401, *1301 |
| 32 | A*0201, *0301; B*3501, *1501; C*0102; *0401 | DRB1*1501, *0701; DQB1*0602, *0303; DPB1*0401 |
| 59 | A*11, *24; B*35, B*40 | n.a. |

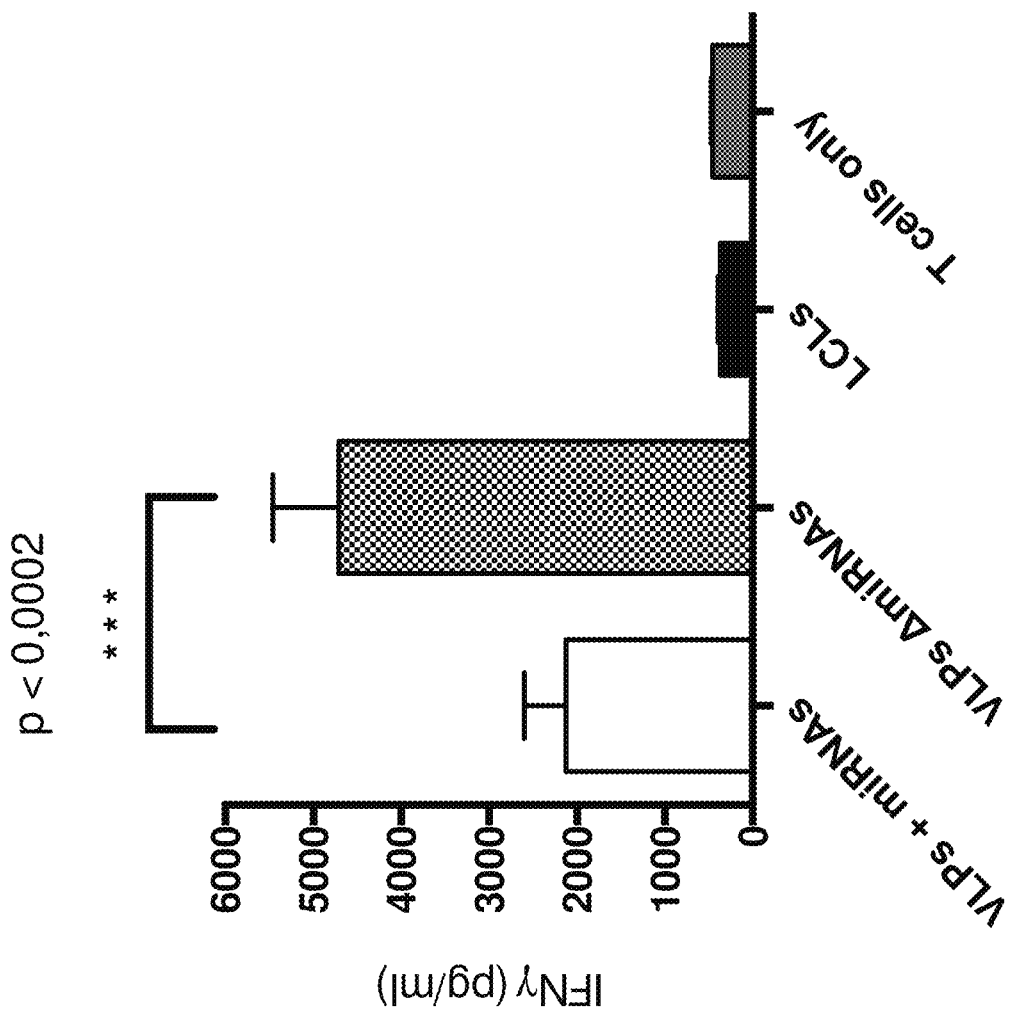

MEANS AND METHODS FOR TREATING HERPESVIRUS INFECTION

CROSS-REFERENCE TO RELATED APPLICATIONS

This application is a continuation of U.S. patent application Ser. No. 16/080,292, filed Aug. 27, 2018, now U.S. Pat. No. 11,602,560, which is a U.S. national phase application of International PCT Patent Application No. PCT/EP2017/054615, which was filed on Feb. 28, 2017, which claims priority to Luxembourg Application No. 93002, filed Mar. 17, 2016, and European Application No. 16000493.3, filed Mar. 1, 2016. These applications are incorporated herein by reference in their entireties.

STATEMENT REGARDING SEQUENCE LISTING

The Sequence Listing XML associated with this application is provided in XML file format and is hereby incorporated by reference into the specification. The name of the XML file containing the Sequence Listing XML is SCHI_008_01US_ST26.xml. The XML file is 31,984 bytes, and created on Mar. 10, 2023, and is being submitted electronically via USPTO Patent Center.

Epstein-Barr virus (EBV) is an oncogenic herpes virus that infects more than 90% of the human population worldwide but causes an enormous threat especially to the immune-compromised host. EBV is responsible for a number of acute and chronic, inflammatory, autoimmune and malignant disorders, which include several types of severe and life-threatening lymphoproliferative diseases in immunosuppressed patients. Patients at risk are candidates for solid organ or hematopoietic stem cell transplantation (SOT/SCT) as well as patients with HIV infection, and patients with congenital immunodeficiency. An important risk factor for EBV-associated PTLD is seronegativity at the time of transplant, which explains particularly high rates of PTLD in children. Depending on the type of transplant, up to 15% of pediatric transplant patients are affected, and eventually 20% of those succumb to the PTLD (Mynarek et al., Clin Dev Immunol. 2013; 2013:814973).

EBV is both ubiquitous and immunogenic. This oncogenic herpes virus (IARC Working Group, *IARC Monogr. Eval. Carcinog. Risks Hum.* 94, 46-70 (2010)) has evolved multiple genes to fend off immune responses when its infection is established (Ressing et al., *Semin. Cancer Biol.* 18, 397-408 (2008)). However, these viral genes do not accumulate immediately on infection of B-lymphocytes, EBV's primary target cells. Thus, early infection should be its Achilles heel, a window when EBV is unprotected from the host's immune response.

A prophylactic vaccine is thought to be the most effective step towards reducing the burden of EBV-associated malignant and non-malignant diseases. Not only PTLD but also infectious mononucleosis (IM) in children and adolescents and endemic Burkitt lymphoma are diseases that were identified as indications of a prophylactic EBV vaccine (Balfour, Curr Opin Virol., 2014, vol. 6, pp. 1-5; Cohen et al., Sci Transl Med., 2011, 3(107):107fs7; Cohen et al., Vaccine, 2013, 31 Suppl 2:6194-6). These diseases are also secondary targets for efficacy trials with the planned VLP vaccine. Epstein made the first vaccine proposal almost 40 years ago, but a viable vaccine is still not available. Progress is significantly hampered by the lack of tractable animal models except subhuman primates and the complexity of the virus. Most vaccine efforts to prevent EBV infection or related diseases have focused on gp350, which is the most abundant glycoprotein of the virion and the principal target of naturally occurring neutralizing antibodies. Vaccination with a soluble form of gp350 reduced the rate of IM in EBV seronegative adults, but had no effect on the rate of EBV infection (Sokal et al., J Infect Dis., 2007, 196(12):1749-53). Another gp350-based vaccine induced antibody responses in EBV-negative children with chronic kidney disease awaiting transplantation, but did not prevent post-transplant adverse consequences of EBV-associated diseases (Rees et al., Transplantation, 2009, 88(8):1025-9). In sum, the few clinical vaccination trials indicate that a prophylactic vaccination against EBV-associated diseases is feasible, but the trials also document that current vaccination strategies need to be considerably improved to prevent primary infection and/or EBV-associated diseases in all vaccinees. Thus, there is an urgent unmet need of a vaccine against EBV.

The present inventors revealed that EBV on infecting primary B-cells efficiently suppresses multiple arms of adaptive immune responses with its encoded miRNAs. They control all three signals required for antigen-specific T-cell activation and recognition: (i) processing and presentation of antigenic peptides to T-cells; (ii) levels of important co-receptors on EBV-infected B-cells that modulate T-cell activation; and (iii) secretion of pro-inflammatory and other cytokines that polarize naive $CD4^+$ T-cells to antiviral Th1 helper cells, thereby miRNAs protect newly infected B-lymphocytes from immune eradication, allowing EBV's life-long success. Namely, the present inventors found that EBV's miRNAs target cellular genes directly to inhibit secretion of cytokines, antigen processing, recognition of virus-infected cells by EBV-specific $CD4^+$ and $CD8^+$ T-cells, and/or differentiation of naïve T-cells to antiviral Th1 cells. The variety and the massive inhibition of adaptive immune responses by multiple miRNAs of a single pathogen was unexpected and unprecedented.

The results obtained by the present inventors can also explain the abundance of miRNAs in complex persisting viruses, and clarify how a human pathogen can evade elimination for the lifetime of its host in spite of intense adaptive immune responses. This global suppression allows the virus to express antigenic functions in cells needed initially to establish its life-long infection evading destruction by T-cells.

By using a human cellular model closely mimicking natural infection the present inventors found that EBV's miRNAs counteract multiple pathways of antiviral adaptive immunity as described in more detail in the appended Examples and illustrated in the Figures.

Given the surprising findings of the present inventors on the prominent role of EBV miRNAs in infection, it would be desirous to eliminate such miRNAs not only from EBV, but also from other herpes viruses to which EBV belongs. In fact, it is known that, apart from EBV, also other herpesviruses have miRNAs which are envisioned to have such prominent role as the miRNAs of EBV as well (Boss et al. 2009, Trends in Microbiology, vol. 17, issue 12, pp. 544-553).

Accordingly, the present invention provides herpesviruses, such as gamma herpes viruses, e.g. EBV, that lack at least one viral miRNA or preferably all viral miRNAs. Such herpesviruses that lack at least one viral miRNA or preferably all viral miRNAs are advantageously also not capable of packaging their genome or the nucleic acid molecule encoding the proteinaceous part of the virus into the capsid, thereby producing herpesvirus-like particles (HVLPs) or Epstein-Barr virus-like particles (EBVLP) which are substantially free of their herpesvirus genome or the nucleic acid molecule encoding the proteinaceous part of the virus and miRNA.

Virus-like particles (VLPs) are structural similar to mature virions but lack the viral genome. Therefore, VLPs are promising candidates for vaccination. Accordingly, such HVLPs end EBVLPs of the present invention may be used as herpesvirus vaccines.

Therefore, the present invention provides a Herpes virus-like particle (HVLP) comprising Herpes viral proteins which are encoded by at least one nucleic acid molecule which still comprises miRNA coding loci encoding Herpes viral miRNAs, wherein at least one of said miRNA coding loci is genetically modified.

The term "Herpes virus-like particle" and "HVLP" are used interchangeably herein and relate to particles, which share morphological and immunological properties with infectious Herpes virus particles, but lack the viral genome and thus are preferably not capable of propagating infection and/or replicating in a suitable host cell. HVLPs in accordance with the present invention can in principle comprise all Herpes viral proteins of the wild type virus and thus preferably have a typical Herpes virus structure as can be analyzed by electron microscopy, i.e. they have a capsid, a tegument and an outer membrane. Thus, a HVLP of the present invention may comprise Herpes viral capsid or capsid precursor proteins, surface proteins, envelope proteins, coat proteins, shell proteins, glycoproteins, tegument proteins, proteins giving rise to B-cell and/or T-cell epitopes. However, certain Herpes virus proteins of the HVLP of the present invention may be genetically modified compared to the wild type virus strain, as described herein. It is however also envisaged that the HVLP lacks one or more non-essential viral proteins. Such a non-essential viral protein is incorporated in the wild type HVLP but is not essential for the formation of the HVLP, as can be detected by electron microscopy of a HVLP produced according to the methods described herein in absence of the polypeptide encoded by said gene. A HVLP of the present invention preferably comprises or consists of proteins originating from one Herpes virus (e.g. Epstein-Barr virus) and even more preferred from one Herpes virus strain, e.g. Epstein-Barr virus strain B95.8, Epstein-Barr virus type 1 or Epstein-Barr virus type 2, Epstein-Barr virus strain B95.8 being preferred.

The term "Herpes viral proteins" as used herein comprises proteins of wild type Herpes virus strains, but also proteins that are not identical to proteins of wild type Herpes virus strains as regards the sequence, but share at least 99%, at least 98%, at least 97%, at least 96%, at least 95%, at least 94%, at least 93%, at least 92%, at least 91%, at least 90%, at least 85%, at least 80%, or at least 75% sequence homology with proteins of wild type Herpes virus strains. By way of example, wild type Epstein-Barr virus proteins are preferably encoded by the prototypic Epstein-Barr virus B95.8 (Genbank Accession number V01555). Moreover, wild type Epstein-Barr virus proteins can be encoded by Epstein-Barr virus type 1 (Genbank Accession number NC_007605.1), or by Epstein-Barr virus type 2 (Genbank Accession number NC_009334.1).

"Sequence identity" or "sequence homology" refers to the percentage of residue matches between at least two polypeptide or polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. For purposes of the present invention, the sequence identity between two amino acid sequences is determined using the NCBI BLAST program version 2.3.0 (Jan. 13, 2016) (Altschul et al., Nucleic Acids Res. (1997) 25:3389-3402). Sequence identity of two amino acid sequences can be determined with blastp set at the following parameters: Matrix: BLOSUM62, Word Size: 3; Expect value: 10; Gap cost: Existence=11, Extension=1; Compositional adjustments: Conditional compositional score matrix adjustment.

A HVLP of the present invention may further comprise in addition to Herpes virus proteins one or more artificial proteins. The term "artificial proteins" as used herein relates to proteins, which are not encoded by the wild type Herpes virus. Artificial proteins may be selected from the group of additional foreign antigenic sequences, cytokines, CpG motifs, g-CMSF, fluorescent proteins, proteins useful for purification purposes of the particles or for attaching a label, proteinaceous structures required for transport processes and others.

The HVLP of the present invention relates to a particle whose proteinaceous part is encoded by the at least one nucleic acid molecule. Accordingly, the at least on nucleic acid molecule may comprise all genes of the wild type Herpes virus and thus encode all Herpes viral proteins of the wild type Herpes virus and may further comprise also all non-coding nucleic acid sequences (e.g. miRNA coding loci, cis-acting elements) of the Herpes virus. Thus, the at least one nucleic acid molecule may comprise all coding and non-coding nucleic acid sequences of the wild type virus. However, certain genes, coding sequences or non-coding sequences of the at least one nucleic acid molecule may be modified compared to the wild type Herpes virus, as described herein. Furthermore, the at least one nucleic acid molecule may lack one or more genes compared to the wild type virus which are not essential for the formation of a HVLP, as can be determined by electron microscopy of a HVLP produced according to the methods described herein in absence of the polypeptide encoded by said gene. The at least one nucleic acid molecule is thus capable of conferring the production of the HVLPs of the present invention in a suitable host cell. By way of example, the at least one nucleic acid molecule which encodes an Epstein-Barr virus-like particle (EBVLP) may comprise all coding and/or non-coding sequences of wild type Epstein-Barr virus (e.g. EBV strain B95.8), which may comprise one or more genetic modifications such as (i) functional inactivation of one or more viral oncogenes required for B-cell transformation (e.g. EBNA1, EBNA-LP, EBNA2, LMP1, LMP2, EBNA3A, and EBNA3C), (ii) functional inactivation of one or more cis-acting elements (e.g. terminal repeats, TR) or viral genes encoding portal proteins (e.g. BFLF1, BBRF1, BGRF1, BDRF1, BALF3, BFRF1A, and BFRF1) which are essential for cleavage and packaging of the at least one nucleic acid molecule, (iii) functional inactivation of one or more viral genes required for inducing virus synthesis (e.g. BZLF1, BRLF1 and BMLF1), and/or (iv) functional inactivation of at least one miRNA coding loci. Thus, in a preferred embodiment of the invention the at least one nucleic acid molecule is one nucleic acid molecule that differs from a wild type EBV genome only with respect to the above identified features. It is however also envisaged that the EBVLP lacks one or more non-essential viral proteins. Such a non-essential viral protein is incorporated in the wild type EBVLP but is not essential for the formation of the EBVLP, as can be detected by electron microscopy of an EBVLP produced according to the methods described herein in absence of the polypeptide encoded by said gene. Furthermore, the at least one nucleic acid molecule preferably comprises or consists of nucleic acid sequences originating from one Herpes virus (e.g. Epstein-Barr virus) and even more preferred from one Herpes virus strain, e.g. Epstein-Barr virus strain B95.8, Epstein-Barr virus type 1 or Epstein-Barr virus type 2, Epstein-Barr virus strain B95.8 being preferred. In a further preferred embodiment of the invention the at least one nucleic acid molecule which encodes the EBVLP does not encode a functional BHRF1 protein.

The terms "Herpes virus genes" and "wild type Herpes virus genes" are used interchangeably herein, comprise genes of wild type Herpes virus strains, but also genes that are not identical to genes of wild type Herpes virus strains as regards the sequence, but share at least 99%, at least 98%, at least 97%, at least 96%, at least 95%, at least 94%, at least 93%, at least 92%, at least 91%, at least 90%, at least 85%, at least 80%, or at least 75% sequence homology with genes of wild type Herpes virus strains. By way of example, wild type Epstein-Barr virus genes are preferably encoded by the prototypic Epstein-Barr virus B95.8. Moreover, wild type Epstein-Barr virus type 1 genes are encoded by Epstein-Barr virus type 1 (Genbank Accession number NC_007605.1), wild type Epstein-Barr virus type 2 genes are encoded by Epstein-Barr virus type 2 (Genbank Accession number NC_009334.1).

Thus, upon expression of the at least one nucleic acid in a suitable host cell the Herpes viral proteins are expressed, resulting in the formation of HVLPs. Consequently, the HVLP of the present invention is obtainable by a host cell which comprises the at least one nucleic acid encoding the Herpes viral proteins which still comprises miRNA coding loci encoding Herpes viral miRNAs, wherein at least one of said miRNA coding loci is genetically modified. However, the HVLP of the present invention is after formation released from the host cells, preferably via the endosomal sorting complex required for transport (ESCRT). Thus, a HVLP of the present invention further comprises cellular components derived from the host cell, such as lipids, proteins, glycoproteins (e.g. CD63), nucleic acids (e.g. mRNAs and miRNAs), cell membranes and others.

The term "cell membranes" as used herein relates to lipids that naturally form cell membranes by spontaneously arranging to form a lipid bilayer, such as amphiphatic phospholipids, wherein after self-assembly the hydrophobic regions of the amphiphatic phospholipids form the inner part of the bilayer whereas the hydrophobic regions form the outer face of the membrane. Preferably, such cell membranes originate from the host cell from which a HVLP of the present invention originates and forms the outer membrane of the HVLP of the present invention. Furthermore, such a cell membrane comprises proteins, e.g. EBV structural proteins such as gp350 and/or LMP-1 in case of an EBVLP.

The term "herpesvirus" as used herein relates to any virus of the family of Herpesviridae. However, preferred are herpesviruses which infect humans such as Human herpesvirus 1 (Herpes simplex virus 1 or HSV-1), Human herpesvirus 2 (Herpes simplex virus 2 or HSV-2), Human herpesvirus 3 (Varicella-zoster virus or VZV), Human herpesvirus 4 (Epstein-Barr virus or EBV), Human herpesvirus 5 (Human cytomegalovirus or HCMV), Human herpesvirus 6, Human herpesvirus 7, Human herpesvirus 8 (Kaposi's sarcoma-associated herpesvirus or KSHV). Even more preferred is the Human herpesvirus 4 (Epstein-Barr virus or EBV), which relates to EBV type 1 and EBV type 2 and preferably EBV strain B95.8. However, also envisioned are Murid herpesvirus 4 (e.g. Murine gammaherpesvirus 68 or MHV-68) and Bovine herpesvirus 1 (e.g. Infectious bovine rhinotracheitis virus).

The terms "protein" or "polypeptide" are used interchangeably herein and refer to a molecule comprising a polymer of amino acids linked together by peptide bonds. Said term is not meant herein to refer to a specific length of the molecule. A polypeptide comprises an amino acid sequence, and, thus, sometimes a polypeptide comprising an amino acid sequence is referred to herein as a "polypeptide comprising a polypeptide sequence". Thus, herein the term "polypeptide sequence" is interchangeably used with the term "amino acid sequence".

The term "amino acid" or "aa" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

The terms "polynucleotide", "nucleotide sequence" "nucleic acid molecule" or "nucleic acid" are used interchangeably herein and refer to a polymeric form of nucleotides, which are usually linked from one deoxyribose or ribose to another. The term "polynucleotide" preferably includes single and double stranded forms of DNA. A nucleic acid molecule may include both sense and antisense strands of RNA (containing ribonucleotides), cDNA, genomic DNA, and synthetic forms and mixed polymers of the above.

The Herpes viral proteins of the HVLP of the invention are encoded by at least one nucleic acid molecule. Thus, the Herpes viral proteins of the HVLP may be encoded by 2, 3, 4, 5, 6, 7, 8, 9, 10, 11, 12, 13, 14, 15, or more nucleic acid molecules. However, in a preferred embodiment of the invention the Herpes viral proteins of the HVLP are encoded by one nucleic acid molecule.

The at least one nucleic acid molecule encoding the Herpes viral proteins still comprises miRNA coding loci encoding Herpes viral miRNAs of the HVLP, wherein at least one of said miRNA coding loci is genetically modified. Such miRNAs coding loci are derived from the Herpes virus and therefore encode viral miRNAs. The term "still comprises" in this context thus means that the miRNA coding loci originate from a Herpes virus, preferably from the same Herpes virus from which the proteins originate, and are still comprised by the at least one nucleic acid molecule encoding the herpes viral proteins. Or in other words, the at least one nucleic acid molecule comprises Herpes viral coding and non-coding nucleic acid sequences including the miRNA coding loci. Such viral miRNAs are usually expressed in the host cell and thus packaged in the viral particle upon virus synthesis. Consequently, the viral miRNAs are as well packaged in the HVLPs upon production of the HVLPs as described herein. However, such viral miRNAs may counteract the antiviral immunity of the host, which may be detrimental upon vaccination with a HVLP. Thus, at least one miRNA coding loci of the at least one nucleic acid molecule, which encodes at least one miRNA, is genetically modified. However, also more than one miRNA coding loci may be genetically modified, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more. In a preferred embodiment of the invention all viral miRNA coding loci are genetically modified. In a further embodiment at least one miRNA coding loci of each miRNA cluster of the Herpes virus is genetically modified (e.g. at least one miRNA coding loci of the BART cluster and at least one miRNA coding loci of the BHRF1 cluster in case of Epstein-Barr virus).

The term "miRNA" as used herein relates to small non-coding single-stranded RNAs of about 21 to 25 nucleotides in length. The 5'-ends of miRNAs, the so-called seed sequences, recognize partially complementary mRNA targets usually within their 3' untranslated regions and repress translational of these mRNAs. miRNA coding loci are first transcribed into longer primary miRNAs (pri-miRNAs) usually by RNA polymerase II. The RNase III enzyme Drosha then recognizes and cleaves the pri-miRNAs to liberate hairpin structures, usually 60 to 80 nt long, called pre-miRNAs, which are transported into cytoplasm and further processed by another RNase III enzyme named Dicer to produce RNA duplexes. The RNA duplexes associate with Argonaute (Ago) proteins, Dicer, and GW182 in RNA-induced silencing complexes (RISC), where they are unwound. Often, at this stage, one strand (the "star strand") is degraded, while the other strand (mature miRNA) is retained. The RISC is guided by the miRNAs to specifically recognize and regulate target mRNAs. Thus, miRNAs are key regulators of a number of biological processes including developmental timing, differentiation and pattering, but also cellular proliferation, cell death, immune response, haematopoiesis, and cellular transformation or oncogenesis. One single miRNA may directly regulate the expression of hundreds of different mRNAs.

By way of example, Herpes viral miRNAs are H1 to H8 and H11 to H18 of Herpes simplex virus 1, H2 to H7 and H9 to H13 and H19 to H25 of Herpes simplex virus 2, miR-UL36-5p, miR-UL36-3p, miR-UL112, miR-US4, miR-US5-1, miR-US5-2, miR-US25-1-5p, miR-US25-1-3p, miR-US25-2-5p, miR-US25-2-3p, miR-US33-3p, miR-UL22A-5p, miR-UL22A-3p, miR-UL70-5p, miR-US33-5p, miR-UL70-3p and miR-UL112-1 of Cytomegalovirus, miR-K1-5p, miR-K2-5p, miR-K3-5p, miR-K3_+1_5, miR-K4-3p, miR-K4-5p, miR-K5-3p, miR-K6-3p, miR-K6-5p, miR-K7-3p, miR-K7-5p, miR-K8-3p, miR-K8-5p, miR-K9-3p, miR-K9-5p, miR-K10a (-3p), miR-K10b-(-3p), miR-K10b_+1_5(-3p), miR-K10b_+1_5(-3p), miR-K11-3p, miR-K12-3p, miR-K12-5p of Kaposi's sarcoma associated virus and Epstein-Barr virus pre-miRNAs miR-BHRF1-1, miR-BHRF1-2, miR-BHRF1-3, miR-BART1, miR-BART2, miR-BART3, miR-BART4, miR-BART5, miR-BART6, miR-BART7, miR-BART8, miR-BART9, miR-BART10, miR-BART11, miR-BART12, miR-BART13, miR-BART14, miR-BART15, miR-BART16, miR-BART17, miR-BART18, miR-BART19, miR-BART20, miR-BART21, miR-BART22, giving rise to four mature BHRF1 miRNAs and 40 BART miRNAs. However, for the Herpes viruses varicella-zoster virus and HHV-7 no miRNAs have been identified so far. Thus, preferred herpesviruses of the invention are Human herpesvirus 1 (Herpes simplex virus 1 or HSV-1), Human herpesvirus 2 (Herpes simplex virus 2 or HSV-2), Human herpesvirus 4 (Epstein-Barr virus or EBV), Human herpesvirus 5 (Human cytomegalovirus or HCMV), Human herpesvirus 6, Human herpesvirus 8 (Kaposi's sarcoma-associated herpesvirus or KSHV). Even more preferred is the Human herpesvirus 4 (Epstein-Barr virus or EBV), which relates to EBV type 1 and EBV type 2 and preferably EBV strain B95.8. In a further embodiment the present invention does not relate to HVLPs derived from Herpes viruses that do not express miRNAs.

The term "genetically modified" with respect to miRNA coding loci, as used herein generally relates to any genetic modification or mutation, which causes a functional inactivation of the viral miRNA, such that the viral miRNA is no longer capable of interfering with translation of the targeted mRNAs. In a preferred embodiment of the invention the nucleotide sequence of the miRNA coding loci is scrambled, such that precursors of the viral miRNAs are transcribed, but not processed further to give rise to functional miRNAs. Without being bound by theory, such a scrambled miRNA coding sequence abrogate expression of mature miRNAs in host cells and thus result in HVLPs that do not contain viral miRNAs or their functional precursors. Such scrambled miRNA coding loci preferably result in primary miRNAs (pri-miRNAs) that have a wrong 3D structure.

The term "wrong 3D structure" as used herein relates to a genetically modified pri-miRNA which is unable to fold into the specific hairpin structures of pri-miRNAs and therefore is not processed to a mature miRNA by the nuclear RNase III enzyme Drosha. However, the miRNA coding loci may also be deleted. Consequently, genetic modifications as used herein effect that at least one Herpes viral miRNA is not expressed or only partially expressed, at least one Herpes viral miRNA does not bind to its target sequence, at least one Herpes viral miRNA, pri-miRNA or a precursor has a wrong 3D structure, at least one precursor of a Herpes viral miRNA is not further processed, at least one Herpes viral miRNA or its precursor are degraded by the cell, at least one Herpes viral miRNA coding loci has a scrambled sequence, at least one Herpes viral miRNA coding loci is deleted, and/or at least one Herpes viral miRNA or its precursor comprises mutations, deletions or insertions. In a preferred embodiment, genetic modifications as used herein effect that at least one Herpes viral miRNA is not expressed or only partially expressed, at least one Herpes viral miRNA does not bind to its target sequence, at least one Herpes viral miRNA, pri-miRNA or a precursor has a wrong 3D structure, at least one precursor of a Herpes viral miRNA is not further processed, at least one Herpes viral miRNA or its precursor are degraded by the cell, at least one Herpes viral miRNA coding loci has a scrambled sequence, and/or at least one Herpes viral miRNA or its precursor comprises mutations or insertions, but no Herpes viral miRNA coding loci is deleted or comprises deletions. Preferably, such genetic modifications do not alter the wild type nucleotide composition and the genomic architecture of the virus. A genetically modified miRNA coding loci can be identified by comparing the nucleotide sequence of said genetically modified miRNA coding loci with the nucleotide sequence of the corresponding miRNA coding loci of the wild type virus, i.e. in case of EBV with the EBV reference strain with Genbank Accession number AJ507799. Thus, a genetic modification of a miRNA coding loci of the present invention causes a deviation from the sequence of the corresponding loci of the wild type virus (e.g. EBV strain AJ507799) and effects that the miRNA is not expressed or only partially expressed, the miRNA does not bind to its target sequence, the miRNA or its precursor has a wrong 3D structure, the miRNA is not further processed, the miRNA or its precursor are degraded by the cell, the miRNA coding loci has a scrambled sequence, the miRNA coding loci is deleted, and/or at least one Herpes viral miRNA or its precursor comprises mutations, deletions or insertions.

The present inventors surprisingly found that miRNAs of Epstein-Barr virus encode functions that are immunosuppressive and repress adaptive immunity responses of the host. Accordingly, the genetic modification of at least one of the miRNA coding loci, comprised by the at least on nucleic acid molecule, leads to an increased immune response when compared to a HVLP comprising Herpes viral proteins which are encoded by at least one nucleic acid that comprises no genetically modified Herpes viral miRNA coding loci, wherein said increase is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 365, 37%, 38%, 39%, 40%, 41%, 42%, 43%, 44%, 45%, 46% 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, 125%, 150%, 175%, 200%, 250%, 300%, 350%, 400%, 450%, 500%, 600%, 700%, 800%, 900%, 1000% or more or preferably at least 5% as determined in the assay as described herein.

The term "assay" as described herein with respect to detection of an increased immune response relates in general to any assay, which is suitable to detect an immune response, preferably of lymphocytes, such as B-cells, T-cells, NKT-cells. By way of example the new synthesis or release of proinflammatory cytokines by immune cells, preferably lymphocytes, such as B-cells, T-cells or any other lymphocyte can be measured, by using a suitable immunological assay, such as a quantitative ELISA (Enzyme-linked Immunosorbent Assay). Such a quantitative ELISA can be used in context with the present invention to measure the cytokine concentration in the supernatant of immune cells, preferably lymphocytes, such as B-cells, T-cells or any other lymphocyte and more preferably B-cells. Cytokines that can be measured in accordance with the present invention are in general all proinflammatory cytokines, e.g. IL-6 and TNF-α and other cytokines, e.g. IL-12 (comprising proteins p35 and p40 encoded by the genes IL12A and IL12B, respectively), IL-12B (comprising two p40 proteins encoded by the gene IL12B) and IL-23 (comprising proteins p40 and p19 encoded by the genes IL12B and IL23A, respectively). In case of IL-12 it is known that several EBV miRNAs inhibit the transcript of the gene IL12B and thus reduce the secretion of cytokines IL12, IL12B and IL23. Accordingly, the increased immune response is preferably measured by measuring the cytokine concentration, using a quantitative ELISA, in the supernatant of B-cells (e.g. IL-12, IL-6, TNF-α) which have been incubated with HVLPs or EBVLPs that lack at least one Herpes virus or EBV miRNA in accordance with the present invention (i.e. the Herpes viral proteins or EBV proteins of the HVLP or EBVLP are encoded by at least one nucleic acid molecule which still comprises miRNA coding loci encoding Herpes viral or EBV miRNAs, wherein at least one of said miRNA coding loci is genetically modified) and compare the measured cytokine concentration to the cytokine concentration measured in the supernatant of B-cells which have been incubated with HVLPs or EBVLPs that do not lack at least one Herpes virus or EBV miRNA, wherein the HVLPs or EBVLPs that do not lack at least one Herpes virus or EBV miRNA are preferably encoded by a nucleic acid molecule comprising miRNA coding loci, which are identical to the wild type virus (i.e. reference strain AJ507799 in case of EBV). The B-cells in the described assay can be incubated for at least 3 h, at least 6 h, at least 9 h, at least 12 h, at least 15 h, at least 18 h, at least 21 h, at least 24 h, at least 27 h, at least 30 h, at least 36 h at least 39 h, at least 42 h, at least 45 h, at least 48 h, at least 54 h, at least 60 h, at least 66 h, at least 72 h, at least 84 h, at least 96 h or more and preferably 24 h or 36 h or more preferably any intermediate between 24 h to 36 h. Furthermore, the new synthesis of cytokines can be measured using quantitative RT-PCR with primers specific for the cytokine transcript (IL-6, TNF-α, IL-12 or other cytokine transcripts). Thus, the increased immune response can be measured for example by measuring the IL-12 transcript of B-cells which have been incubated with HVLPs or EBVLPs as described herein by using quantitative RT-PCR with IL-12 and preferably IL-12B transcript specific primers and by comparing the results obtained from B-cells which have been incubated with HVLPs or EBVLPs that lack at least one Herpes virus or EBV miRNA in accordance with the present invention and from B-cells which have been incubated with HVLPs or EBVLPs that do not lack at least one Herpes virus or EBV miRNA, wherein said HVLPs or EBVLPs that do not lack at least one Herpes virus or EBV miRNA are preferably encoded by a nucleic acid molecule comprising miRNA coding loci, which are identical to the wild type virus (i.e. reference strain AJ507799 in case of EBV). Moreover, the assay can be an assay, which uses immune cells, preferably lymphocytes, such as T-cells, NKT-cells, or other lymphocytes as a read-out to measure an increased immune response. Such immune cells, termed effector cells, recognize the B-cells incubated with HVLPs or EBVLs (i.e. B-cells that present antigenic epitopes derived from HVLPs or EBVLs). After epitope recognition, the immune cells respond with an increased secretion of cytokines or even kill the B-cells incubated with HVLPs or EBVLPs. Thus, the increased immune response can be measured for example by measuring the cytokine concentration in the supernatant of immune effector cells (e.g. GM-CSF or IFN-gamma), which have been incubated with B-cells incubated with HVLPs or EBVLPs that lack at least one Herpes virus or EBV miRNA compared to the cytokine concentration in the supernatant of immune effector cells, which have been incubated with B-cells incubated with HVLPs or EBVLPs that do not lack at least one Herpes virus or EBV miRNA, wherein said HVLPs or EBVLPs that do not lack at least one Herpes virus or EBV miRNA are preferably encoded by a nucleic acid molecule comprising miRNA coding loci, which are identical to the wild type virus (i.e. reference strain AJ507799 in case of EBV). The increased immune response can further be measured by measuring the release of cytokines by effector cells by staining their surface for cytokines being secreted. The increased immune response of the effector cells can also be measured by measuring the killing of the B-cells incubated with HVLPs or EBVLs. Prior to the killing experiment, B-cells incubated with HVLPs or EBVLPs that lack at least on viral miRNA and B-cells incubated with HVLPs or EBVLPs that do not lack at least on viral miRNA are stained with a dye (e.g. Calcein-acetoxymethlester). Calcein is released to the supernatant upon effector cell-mediated killing, where its concentration is proportional to the number of killed cells and can be quantified by fluorometric measurement. Thus, an increase of Calcein is indicative of an increased immune response. Consequently, an increased immune response can be measured by comparing the Calcein concentration in the supernatant of B-cells, incubated with HVLPs or EBVLPs that lack at least on viral miRNA and B-cells incubated with HVLPs or EBVLPs that do not lack at least on viral miRNA, wherein said HVLPs or EBVLPs that do not lack at least one Herpes virus or EBV miRNA are preferably encoded by a nucleic acid molecule comprising miRNA coding loci, which are identical to the wild type virus (i.e. reference strain AJ507799 in case of EBV).

The term "increased immune response", as used herein relates to an increased immune response upon administration of HVLPs of the present invention to a subject or in an in vitro assay. Such an increase becomes evident when comparing the immune response caused by the HVLP of the present invention with the immune response caused by a HVLP comprising Herpes viral proteins, which are encoded by at least one nucleic acid which does not comprise miRNA coding loci encoding Herpes viral miRNAs that are genetically modified. Such an increased immune response in a subject is preferably an increased adaptive immune response such as a humoral or a cellular immune response, i.e. a B-cell response or T-cell response. More preferably said increased immune response is an increased T-cell response, such as a CD8+ or CD4+ T-cell response. Even more preferred is an increased CD8+ T-cell response. Most preferably, said increased immune response is an increased B-cell, CD4+ T-cell and CD8+ T-cell response. In case of EBVLPs such a CD8+ T-cell response is surprising as EBVLPs are inactivated vaccines, which are known not to induce a CD8+ T-cell response. Thus, upon internalization of an EBVLP of the present invention, one would have expected only a CD4+ T-cell response but not a CD8+ T-cell response.

The term "subject" as used herein relates to an animal, preferably a mammal and more preferably a human.

In a further embodiment of the invention the at least one nucleic acid encoding said Herpes viral proteins is genetically modified such that it is not packaged in the HVLPs. Usually, Herpes viruses comprise cis-acting element and proteins which are required for packaging of the virus genome in the virus particle. Exemplarily, Herpes viruses comprise sequences at both ends of the viral DNA in its linear confirmation which are involved in packaging, such as the "terminal repeats" (TR) of Epstein-Barr virus and Kaposi's sarcoma-associated virus or the "a sequence" of Human cytomegalovirus and Herpes simplex virus 1. By way of example, proteins involved in packaging of the virus genome are BFLF1, BBRF1, BGRF1, BDRF1, BALF3, BFRF1A, and BFRF1 in case of Epstein-Barr virus, UL6, UL15, UL17, UL25, and UL28 in case of Herpes simplex virus 1, UL6, UL15, UL17, UL25, UL28, UL32 and UL33 UL51 in case of Herpes simplex virus 2, UL56 and UL89 in case of Human cytomegalovirus, ORF54 in case of varicella-zoster virus and ORF7, ORF29 and ORF43 in case of Kaposi's sarcoma-associated virus. Accordingly, functional inactivation of one or more of the cis-acting elements and/or proteins required for packaging of the viral DNA results in an impaired packaging of the nucleic acid molecule and thus results in the production of HVLPs upon induction of the lytic phase as described herein.

The term "packaging" is well-known in the art with regard to virus assembly and relates to the process of introducing the linear Herpes viral DNA into the Herpes virus particle during virus particle assembly and specifically relates herein to the process of introducing the at least one nucleic acid molecule into the virus particle during virus particle assembly.

Thus, in a preferred embodiment of the invention the at least one nucleic acid encoding said Herpes viral proteins lacks a functional cis-acting element required for packaging. The term "cis-acting element required for packaging" as used herein relates to Herpes viral DNA packaging-signal sequences, which are required for packaging of the viral DNA in the virus particle. Consequently, in absence of the cis-acting element the at least one nucleic acid molecule is not packaged upon virus synthesis during the lytic phase of the virus into a wild type virus particle or a HVLP of the invention.

In a further preferred embodiment of the invention the at least one nucleic acid encoding said Herpes viral proteins comprises at least one gene encoding a Herpes viral protein required for packaging, which is genetically modified such that said Herpes viral protein is not expressed or non-functional, i.e. the protein required for packaging loses its packaging capacity. Thus, the gene encoding the Herpes viral protein required for packaging may be genetically modified such that the packaging capacity of the protein is functionally disabled while the immunogenicity is preferably maintained. While it may be sufficient to modify one cis-acting element or protein required for packaging such that it is functionally disabled, one can alternatively disable the packaging capacity of a combination of proteins and cis-acting elements to exclude the possibility of viral DNA packaging.

The term "genetically modified" as used herein with respect to nucleic acid sequences encoding Herpes viral proteins generally relates to any genetic modification that renders a virus encoded protein non-functional or prevents expression of such a protein. By way of example, such a genetic modification may be deletion of a nucleic acid sequence encoding the functional domain or parts thereof or the entire protein. A nucleic acid sequences encoding Herpes viral proteins may further be genetically modified by insertion, deletion or substitution of one or more nucleotides encoding for one or more amino acids of the protein, preferably encoding the functional domain of the protein. Such a modification introduces point mutations in the coding sequence generating e.g. a stop codon or a shift of the open reading frame and thus results in a truncated protein. Such a modification may further result in a protein with no or reduced biological function. Furthermore, expression of the gene encoding the Herpes viral protein may also be inhibited by other genetic modifications, e.g. deletion or substitution of nucleotides of the start codon (i.e. the start codon is no longer present) of the open reading frame of the gene or functionally inactivating the promoter sequence or other regulatory nucleic acid sequences required for gene expression and other methods well-known in the art.

Accordingly, in a further embodiment the HVLP of the present invention is substantially free of a Herpes virus genome and/or the at least one nucleic acid molecule. The term "substantially free of a Herpes virus genome and/or the at least one nucleic acid molecule" as used herein relates to HVLPs that comprise less than 1000 Herpes virus genomes or nucleic acid molecules per 1 ml supernatant, less than 100 Herpes virus genomes or nucleic acid molecules per 1 ml supernatant, less than 10 Herpes virus genomes or nucleic acid molecules per 1 ml supernatant, less than 1 Herpes virus genomes or nucleic acid molecules per 1 ml supernatant, less than 0.1 Herpes virus genomes or nucleic acid molecules per 1 ml supernatant, less than 0.01 Herpes virus genomes or nucleic acid molecules per 1 ml supernatant, as can be easily determined by a person skilled in the art using quantitative PCR. Preferably the detection via quantitative PCR comprises an incubation step with DNAse in order to remove free DNA or membrane associated DNA. Accordingly, the HVLPs are preferably substantially free of DNA sequences that are identical to Herpes virus DNA sequences, wherein said sequences preferably relate to Herpes virus gene sequences. Furthermore, the HVLPs are preferably substantially free of nucleic acid sequences that share at least a (for each value) 99%, 98%, 97%, 96%, 95%, 90%, 85%, 80% and at least 75% sequence identity to a wild type Herpes virus nucleic acid sequence. By way of example, HEK293 cells transfected with a B95.8 EBV genome that lacks the TR element and the BZLF1 coding region are transfected with an expression vector encoding BZLF1 in order to induce the lytic phase. Three days later the supernatant can be harvested and EBVLPs can be precipitated by ultracentrifugation. The number of EBV genomes can be quantified via quantitative RT-PCR using primers specific for an EBV gene comprised by said B95.8 genome and by the reference EBV genome. As a reference for quantification one can use a serial dilution of Namalwa DNA, a human Burkitt's lymphoma cell line that contains two EBV genome copies per cell. The quantification of EBV genome copies in EBVLPs is further described in WO2013/098364, whereas sensitivity of the described quantification can be increased by using more than one ml supernatant. In a preferred embodiment the HVLPs of the present invention comprise no detectable viral genomes, wherein the method for detection is quantitative PCR.

However, as described herein at least one gene of the Herpes virus encoding for a protein that is required for inducing virus synthesis may be genetically modified such that said Herpes viral protein (e.g. BZLF1 in case of EBV) is not expressed or non-functional. In this case said at least one gene has to be provided to the host cell in order to induce virus synthesis for production of the HVLPs of the present invention. The at least one gene may be provided by transfecting an expression vector comprising the at least one gene into the host cell. Thus, without being bound by theory, it may be the case that the HVLPs of the present invention comprise the expression vector encoding for said at least one gene. However, it is to be understood, that the terms "substantially free of a Herpes virus genome" and "substantially free of the at least one nucleic acid molecule" do not relate to an expression vector encoding the at least one gene required for inducing virus synthesis.

In another embodiment or the invention the at least one nucleic acid molecule encoding said Herpes viral proteins comprises at least one gene encoding a Herpes viral protein required for cellular transformation, which is genetically modified such that said Herpes viral protein is not expressed or non-functional.

Some Herpes viruses, such as Epstein-Barr virus and Kaposi's sarcoma-associated herpesvirus are known to cause cellular transformation and thus induce neoplastic diseases. In order to increase the safety of a composition comprising a HVLP of the invention upon administration to a subject, at least one gene encoding a herpesviral protein required for cellular transformation may be genetically modified such that said Herpes viral protein is not expressed or non-functional. Thus, the gene encoding the herpesviral protein required for cellular transformation may be genetically modified such that the transformation capacity of the protein is functionally disabled while the immunogenicity is preferably maintained. While it may be sufficient to modify one protein required for cellular transformation it may be preferable to modify more than one protein, such as 2, 3, 4, 5, 6, 7, 8, 9, 10, or more proteins required for cellular transformation in order to exclude the possibility of cellular transformation. Herpes virus genes, which are required for cellular transformation are well-known in the art. By way of example, such genes are EBNA1, EBNA-LP, EBNA2, LMP1, LMP2, EBNA3A, and EBNA3C in case of Epstein-Barr virus and LANA, K13, Kaposin A, Kaposin B, Kaposin C, K1, vIL-6, vIRF-1, and vGPCR in case of Kaposi's sarcoma-associated herpesvirus.

In a further embodiment of the invention the at least one nucleic acid molecule encoding said Herpes viral proteins comprises at least one gene encoding a Herpes viral protein required for inducing virus synthesis, which is genetically modified such that said Herpes viral protein is not expressed or non-functional.

The life cycle of a Herpes virus comprises a latent phase in which only a reduce set of viral genes is expressed and no progeny virus is produced, and a lytic phase in which viral synthesis occurs and progeny virus is released from the host cell. During lytic replication different classes of lytic genes are expressed and the viral genome is amplified to form so-called concatamers, which are eventually cleaved in unit-length linear viral genomes that are packaged in preformed procapsids. Capsids containing viral DNA will undergo further conformational and structural changes and egress from the infected cell as enveloped viral particles. Thus, the lytic phase of the virus life cycle is the process that leads to intracellular assembly of viral particles. However, in case the at least one nucleic acid molecule encoding the proteinaceous part of the HVLP lacks one or more cis-acting elements and/or proteins required of packaging, as described herein, no viral DNA is packaged upon assembly of the viral particle and thus HVLPs are produced upon induction of the lytic phase.

The lytic phase of a Herpes virus is induced and maintained upon expression of certain Herpes viral proteins, e.g. BZFL1, BRLF1 and BMLF1 in case of Epstein-Barr virus, RTA in case of Kaposi's sarcoma-associated virus, VP16 in case of Herpes simplex virus.

As a further safety measure it may be desirable to genetically modify one or more genes encoding a protein required for induction of the lytic phase and thus prevent viral replication from possible residual viral genomes. Thus, the gene encoding the herpesviral protein required for inducing virus synthesis may be genetically modified such that the lytic induction capacity of the protein is functionally disabled while the immunogenicity is preferably maintained.

In case one or more genes required for virus synthesis are functionally inactivated or deleted, said one or more genes have to be provided to the host cell comprising the at least one nucleic acid molecule in order to induce the lytic phase of the virus and thus virus synthesis and thus confer production of the HVLPs of the invention. Said one or more genes may be provided to the host cell by transfecting an expression vector comprising said one or more genes, wherein the expression vector is preferably a stable expression vector and wherein the expression of the one or more genes required for induction of the lytic phase is preferably inducibly regulated.

The term "inducibly regulated" or "induced expression" as used herein relates to any method allowing to induce the expression of a gene at will, e.g. by using tetracycline inducible promoters, Dox-inducible promoters, ecdysone inducible promoters or heavy metal inducible promoters. Further suitable promoters are well-known to the person skilled in the art. Alternatively, expression can also be regulated when by fusing the protein coding sequence to the estrogen receptor coding sequence and thus allow activation upon the addition of estrogen.

In a further embodiment of the invention the at least one nucleic acid molecule encoding the Herpes viral proteins comprises a Herpes virus genome, wherein said Herpes virus is selected from the group consisting of Herpes-simplex virus 1, Herpes-simplex virus 2, Varicella-zoster virus, Epstein-Barr virus, Human cytomegalovirus, Kaposi's sarcoma-associated herpesvirus, Human herpesvirus 6, Human herpesvirus 7, Bovine herpesvirus 1, Bovine herpesvirus 2, Bovine herpesvirus 3, Bovine herpesvirus 4, Bovine herpesvirus 5, and Murine gammaherpesvirus 68.

Accordingly, the at least one nucleic acid molecule may comprise or consist of a Herpes virus genome. However, the Herpes virus genome may be genetically modified compared to a wild type Herpes virus genome as described herein.

In a further embodiment of the invention the HVLP is an Epstein-Barr VLP (EBVLP), comprising Epstein-Barr virus (EBV) proteins and EBV miRNAs.

By way of example, EBV polypeptides comprised in the particle belong to the groups of EBV structural polypeptides and EBV lytic polypeptides. As will be understood by the skilled person, a particular polypeptide of EBV may belong to more than one of the above mentioned groups of polypeptides. In other words, an EBV polypeptide may represent a structural polypeptide as well as a lytic polypeptide. In accordance with the invention, a structural polypeptide of EBV relates to polypeptides involved in the structural setup of the EBV. Said polypeptides are preferably selected from the group consisting of membrane polypeptides, tegument polypeptides and capsid polypeptides. EBV membrane polypeptides comprise the polypeptides selected from the group consisting of BALF4, BLLF1 (also termed gp350), BDLF2, BDLF3, BKRF2, BLRF1, BNLF1 (also termed LMP-1), TP (also termed LMP-2a), BXLF2, BZLF2, and any combination thereof. EBV tegument polypeptides comprise the polypeptides selected from the group consisting of BBRF2, BGLF2, BMLF1, BNRF1, BOLF1, BPLF1, BTRF1, BVRF1, and any combination thereof. EBV capsid polypeptides comprise the polypeptides selected from the group consisting of BBRF1, BcLF1, BDLF1, BFRF3, and any combination thereof. A lytic polypeptide of EBV relates to EBV polypeptides that are involved in the induction and maintenance of the EBV lytic phase and/or are expressed as a consequence of the induction of the lytic phase. Said lytic polypeptides are preferably selected from the group comprising the immediate early genes, the early genes and the late lytic genes (Kieff and Rickinson, 2007). The lytic phase is initiated by the expression of BZLF1 and BRLF1, both immediate early proteins, followed by the expression of the early and late proteins. Following induction, cells that have become permissive for virus replication undergo cytopathic changes characteristic of herpesviruses (Kieff and Rickinson, 2007).

The invention also relates to an EBVLP comprising EBV proteins which are encoded by at least one nucleic acid molecule which still comprises miRNA coding loci encoding EBV miRNAs, wherein at least one of said miRNA coding loci is genetically modified, wherein said at least one miRNA coding loci is selected from the group consisting of miR-BHRF1-1, miR-BHRF1-2, miR-BHRF1-3, miR-BART1, miR-BART2, miR-BART3, miR-BART4, miR-BART5, miR-BART15. Any other miRNA coding loci of EBV can be present in an unmodified form (i.e. identical to reference strain AJ507799 in case of EBV) or can be deleted.

In case of an EBVLP the at least one genetically modified miRNA coding loci encoding EBV miRNAs, which is comprised by the at least one nucleic acid molecule, is selected from the group consisting of miR-BHRF1-1, miR-BHRF1-2, miR-BHRF1-3, miR-BART1, miR-BART2, miR-BART3, miR-BART4, miR-BART5, miR-BART15. Accordingly, at least one, at least 2, at least 3, at least 4, at least 5, at least 6, at least 7, at least 8 of said miRNA coding loci can be genetically modified in any possible combination. In a preferred embodiment of the invention all of said EBV miRNA coding loci are genetically modified as described herein. Thus, the present invention does not relate to EBV strain B95.8 (Genbank Accession number V01555). However, the present invention relates to any EBV strain B95.8 which comprises a genetic modification of at least one miRNA coding loci as described herein. In a further embodiment of the invention in case of an EBVLP the at least one genetically modified miRNA coding loci encoding EBV miRNAs, which is comprised by the at least one nucleic acid molecule, is selected from the group consisting of miR-BHRF1-1, miR-BHRF1-2, miR-BHRF1-3, miR-BART1, miR-BART2, miR-BART3, miR-BART4, miR-BART15. In an even further preferred embodiment all EBV miRNA coding loci, as described herein, are genetically modified.

As a feature that increases safety upon administration of an EBVLP of the invention, e.g. upon vaccination, at least one gene, comprised by the at least one nucleic acid molecule, encoding an EBV protein required for B-cell transformation, selected from the group consisting of EBNA1, EBNA-LP, EBNA2, LMP1, LMP2, BHRF1, BALF1, EBNA3A, and EBNA3C, is genetically modified such that the EBV protein is not expressed or non-functional.

The term "required for B-cell transformation" means in accordance with the invention that the said one or more EBV polypeptides are essential in transforming B-cells upon infection with a wild type EBV. In other words, in the absence of said one or more essential EBV polypeptides a B-cell is not transformed upon infection. Accordingly, the EBVLP upon fusion with the B-cell is incapable of transforming the B-cell. While it may suffice to disable the B-cell transformation capacity of one essential EBV polypeptide, in order to exclude the possibility of B-cell transformation, one can alternatively disable the B-cell transformation capacity of an essential combination of EBV polypeptides to achieve the same result achieved when only one essential polypeptide is disabled, i.e. achieve the exclusion of the possibility of B-cell transformation. Preferably, the B-cell transformation capacity of more than the one essential EBV polypeptide or the essential combination of EBV polypeptides is disabled. A corresponding EBV polypeptide that is essential in B-cell transformation is EBNA2 and a combination of EBV polypeptides essential in B-cell transformation is the combination of BHRF1 and BALF1. Disabling the B-cell transformation capacity of EBNA2 or of BHRF1 and BALF1 is sufficient to exclude the possibility of B-cell transformation. Further EBV polypeptides and combinations of EBV polypeptides that are required for B-cell transformation are LMP1, EBNA3A and EBNA3C, EBNA1 and EBNA3A, or EBNA-LP and EBNA3C. In one embodiment the EBV genes EBNA2, LMP1, EBNA1, EBNA3A, and EBNA3C are genetically modified such that the EBV proteins are not expressed or non-functional. In a further embodiment all of said genes are genetically modified such that the EBV proteins are not expressed or non-functional.

In a further embodiment of the invention at least one gene, comprised by the at least one nucleic acid molecule, encoding an EBV protein required for inducing virus synthesis, selected from the group consisting of BZFL1, BRLF1 and BMLF1, is genetically modified such that the EBV protein is not expressed or non-functional, wherein said gene is preferably BZLF1.

As a further safety measure it may be desirable to genetically modify one or more genes encoding a protein required for induction of the lytic phase (used interchangeably herein with the terms "replicative phase") and thus prevent virus synthesis from possible residual viral genomes. By way of example, the EBV immediate early polypeptide BZLF1 mediates the disruption of latent EBV infection and is generally considered the key regulator in the induction of the lytic phase of EBV. The persistent infection with EBV is characterized in that there is an alternation of lytic and latent phase, wherein the induction of the lytic phase is due to the expression of BZLF1. Accordingly, upon deletion or functionally inactivating BZLF1 induction of the lytic phase of EBV is prevented. Consequently, said one or more genes which have been deleted or functionally inactivated, such as BZLF1, have to be provided to the host cell comprising the at least one nucleic acid molecule in order to induce the lytic phase of EBV and thus virus synthesis and thus confer production of the EBVLPs of the invention. Said one or more genes may be provided to the host cell by transfecting an expression vector comprising said one or more genes, wherein the expression vector is preferably a stable expression vector and wherein the expression of the one or more genes required for induction of the lytic phase is preferably inducibly regulated.

The at least one nucleic acid encoding the EBV proteins may be modified by deleting or functionally inactivating a cis-acting element such that the at least one nucleic acid is not packaged in the EBVLPs. In a preferred embodiment of the invention the at least one nucleic acid molecule encoding said EBV proteins lacks the packaging element TR. The packaging of EBV genomic DNA initiates at the terminal repeats (TR) that are directly repeated at both ends of the viral genome in its linear state. Said terminal repeats are recognized by an enzyme termed "terminase". Thus, the at least one nucleic acid molecule or an EBV genome is not packaged into the procapsid of EBV if it lacks the packaging element TR, resulting in the production of the EBVLP of the present invention. In case the at least one nucleic acid molecule or the EBV genome used in the production of the EBVLP lacks the packaging element TR, the EBV gene BALF4 may not be co-expressed in the host cell used in the production of the EBVLP.

In a further embodiment of the invention the at least one nucleic acid molecule encoding the EBV proteins comprises at least one gene encoding an EBV protein required for packaging of EBV DNA, selected from the group consisting of BFLF1, BBRF1, BGRF1, BDRF1, BALF3, BFRF1A, and BFRF1, which is genetically modified such that said EBV protein is not expressed or non-functional, wherein BFRF1A is preferred. The proteins of said genes are required for packaging of viral DNA (i.e. an EBV genome or the at least one nucleic acid molecule) into procapsids of EBV. Accordingly, the at least one nucleic acid molecule or an EBV genome is not packaged in the into the procapsid of EBV if one or more of said genes are genetically modified such that said EBV protein is not expressed or non-functional and thus results in the production of the EBVLP of the present invention.

In a further embodiment of the invention the at least one nucleic acid molecule encoding said EBV proteins comprises an EBV genome. In this case, the at least one nucleic acid molecule encoding the EBVLP may comprise or consist of an EBV genome, which may be genetically modified compared to a wild type EBV genome as described herein and wherein the at least one nucleic acid molecule encoding the EBVLP still comprises EBV encoded miRNAs.

Exemplarily, the publications Delecluse et al. (PNAS, vol. 96, pp. 5188-5193, 1999) and Ruiss et al. (Journal of Virology, pp. 13105-13113, 2011) of the present inventors and the documents WO2012/025603 and WO2013/098364 disclose nucleic acid molecules that confer the production of an EBVLP upon expression in a suitable cell line, e.g. HEK293 cells. Said nucleic acid molecules have been modified in accordance with the present invention but still comprise miRNA encoding loci. Accordingly, a nucleic acid molecule of the present invention can be obtained by using one of said nucleic acid molecules disclosed in the publications and documents cited above and deleting at least one miRNA encoding loci as described herein, wherein the obtained nucleic acid molecule can be further modified as described herein.

The present invention further pertains to a nucleic acid molecule encoding the Herpes viral proteins of the HVLP or the EBV proteins of the EBVLP. The present invention also pertains to a vector comprising the nucleic acid molecule encoding the Herpes viral proteins of the HVLP or the EBV proteins of the EBVLP.

The term "vector" as used herein with respect to the at least one nucleic acid molecule encoding the Herpes virus proteins or the EBV proteins refers to a nucleic acid sequence into which one or more expression cassettes comprising a gene encoding the protein of interest may be inserted or cloned. Furthermore, the vector preferably encodes an antibiotic resistance gene conferring selection of the host cell and/or a phenotypical marker, e.g. a fluorescent protein, such as GFP, RFP, YFP, BFP or others. Preferably, the vector is a plasmid or viral vector. The vector can contain elements for propagation in bacteria (e.g. *E. coli*), yeast (e.g. *S. cerevisiae*), insect cells and/or mammalian cells. Preferably, said vector comprises a bacterial mini-F-factor plasmid element, allowing propagation in *E. coli*.

In a further embodiment the present invention provides a composition of matter comprising at least two nucleic acid molecules encoding the Herpes viral proteins of the HVLP or the EBV proteins of the EBVLP. In an even further embodiment of the present invention the at least two nucleic acid molecules are comprised by at least two vectors (i.e. two nucleic acid molecules are comprised by two vectors, three nucleic acid molecules are comprised by three vectors, four nucleic acid molecules are comprised by four vectors, etc.).

The present invention further provides a host cell transfected with the nucleic acid molecule encoding the Herpes viral proteins of the HVLP or the EBV proteins of the EBVLP or the vector comprising said nucleic acid molecule or the composition of matter comprising at least two nucleic acid molecules encoding the Herpes viral proteins of the HVLP or the EBV proteins of the EBVLP, wherein the at least two nucleic acid molecules are preferably comprised by at least two vectors.

The term "host cell" as used herein relates to a cell, which allows lytic replication of the Herpes virus or EBV resulting in the formation of HVLPs or EBVLPs. Such a host cell is preferably a mammalian cell, more preferably a primate cell, even more preferably a human cell and most preferably a HEK293 cell. In case the Herpes virus or EBV lack one or more functional proteins required for inducing virus synthesis (i.e. the lytic phase), it is envisioned that the host cell may provide the one or more proteins (e.g. BZLF1 in case of EBV). The host cell may provide the one or more proteins via a transfected vector, a stably transfected vector or by chromosomal integration of the nucleic acid sequence encoding the one or more proteins, wherein expression of said one or more proteins is preferably inducibly regulated.

The term "transfection" as used herein relates to the process of introducing nucleic acids into cells. Transfection can be achieved by a variety of methods such as, e.g. chemical-based methods like calcium phosphate-mediated transfection or liposome-mediated transfection (lipofection). Also non-chemical methods like electroporation or sonoporation or particle-based methods such as gene-gun-mediated transfection or magnetofection as well as viral-mediated methods are known in the art.

The present invention further pertains to a method for generating a HVLP or an EBVLP, the method comprising:
(i) culturing the host cell under conditions that allow expression of the Herpes viral proteins or the EBV proteins; and
(ii) obtaining said HVLP or EBVLP.

The present invention further relates to a HVLP or an EBVLP obtainable by the method for generating a HVLP or an EBVLP of the present invention. The present invention also relates to a vaccine comprising a HVLP or an EBVLP obtainable by the method for generating a HVLP or an EBVLP of the present invention.

The method of the present invention is preferably an in vitro method. Exemplarily, the generation of EBVLPs is disclosed in the publications Delecluse et al. (PNAS, vol. 96, pp. 5188-5193, 1999) and Ruiss et al. (Journal of Virology, pp. 13105-13113, 2011) of the present inventors and in the documents WO2012/025603 and WO2013/098364.

The term "culturing" as used herein relates to growing cells outside the organism in cell culture medium and is known by the person skilled in the art. Suitable cell culture media confer survival and replication by the cells and are commercially available. They may comprise nutrients, salts, growth factors, antibiotics, serum (e.g. fetal calf serum) and pH-indicators (e.g. phenol red).

The term "obtaining" as used herein relates to isolating and/or purifying the HVLPs or EBVLPs, preferably from the cell culture supernatant. Such isolation and/or purification steps are known to the person skilled in the art and encompass for example methods such as density gradient centrifugation, size-exclusion chromatography, affinity chromatography, precipitation and in case of EBV by binding EBVLP to magnetic beads via anti-gp350 antibodies.

The method of the present invention may further comprise after step (i) and prior to step (ii) a further step (i'), comprising inducing the replicative phase of the Herpes virus or Epstein-Barr virus, wherein said replicative phase is induced by expressing at least one gene, encoding a Herpes viral protein or an EBV protein that is required for inducing Herpes virus synthesis or EBV synthesis, wherein said Herpes viral protein or EBV protein has been genetically modified in the at least one nucleic acid molecule encoding the Herpes viral proteins of the HVLP or the EBV proteins of the EBVLP, such that it is not expressed or non-functional.

In a further embodiment of the method of the present invention the at least one gene encoding a Herpes viral protein or an EBV protein that is required for inducing Herpes virus synthesis or EBV synthesis is expressed from a stably transfected vector in said host cell and/or wherein said gene is inducibly regulated. In a further preferred embodiment of the method of the present invention the at least one gene encoding an EBV protein that is required for inducing EBV synthesis is selected from the group consisting of BZLF1, BRLF1 and BMLF1, wherein BZLF1 is preferred.

In a further embodiment the present invention relates to a composition comprising at least 99.99%, 99.9%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 65%, 60%, 55%, 50%, 45%, 40%, 35%, 30%, 25%, 20%, 15%, 10%, 5% or preferably 95% of the HVLP or the EBVLP as defined herein. Accordingly, such a composition may further comprise, irrespective of the comprised HVLPs or the EBVLPs as described herein, HVLPs or EBVLPs that are not in line with the description herein, e.g. such a composition may comprise defect HVLPs or EBVLPs that are not morphologically similar to a virus particle, as can be determined using electron microscopy.

In another embodiment the present invention pertains to a vaccine composition comprising the HVLP or the EBVLP as described herein or the composition comprising the HVLPs or the EBVLPs as described herein.

The terms "vaccine" and "vaccine composition" are used interchangeably herein and relate to a composition comprising HVLPs or EBVLPs of the present invention which—when administered to a subject—elicits an immune response against the Herpes virus or EBV. Thus, administering said vaccine composition to a subject stimulates the immune system and establishes or improves immunity to a new and/or persisting infection with the Herpes virus or EBV. Preferably, the vaccine according to the present invention allows for establishing or improving immunity to a new and/or persisting infection with EBV. Preferably, the immunization causes activation and expansion of T-cells and/or B-cells specifically recognizing EBV antigens, e.g. EBV structural antigens. Even more preferably, the immunization causes activation and expansion of CD8+ T-cells. It is also preferred that, immunization causes the production of antibodies preventing infection of body cells by EBV.

In a further embodiment the vaccine composition of the present invention further comprises an excipient.

The terms "carrier" and "excipient" are used interchangeably herein. Pharmaceutically acceptable carriers include, but are not limited to diluents (fillers, bulking agents, e.g. lactose, microcrystalline cellulose), disintegrants (e.g. sodium starch glycolate, croscarmellose sodium), binders (e.g. PVP, HPMC), lubricants (e.g. magnesium stearate), glidants (e.g. colloidal SiO2), solvents/co-solvents (e.g. aqueous vehicle, Propylene glycol, glycerol), buffering agents (e.g. citrate, gluconates, lactates), preservatives (e.g. Na benzoate, parabens (Me, Pr and Bu), BKC), anti-oxidants (e.g. BHT, BHA, Ascorbic acid), wetting agents (e.g. polysorbates, sorbitan esters), anti-foaming agents (e.g. Simethicone), thickening agents (e.g. methylcellulose or hydroxyethylcellulose), sweetening agents (e.g. sorbitol, saccharin, aspartame, acesulfame), flavouring agents (e.g. peppermint, lemon oils, butterscotch, etc), humectants (e.g. propylene, glycol, glycerol, sorbitol). Further pharmaceutically acceptable carriers are (biodegradable) liposomes; microspheres made of the biodegradable polymer poly(D, L)-lactic-coglycolic acid (PLGA), albumin microspheres; synthetic polymers (soluble); nanofibers, protein-DNA complexes; protein conjugates; erythrocytes; or virosomes. Various carrier based dosage forms comprise solid lipid nanoparticles (SLNs), polymeric nanoparticles, ceramic nanoparticles, hydrogel nanoparticles, copolymerized peptide nanoparticles, nanocrystals and nanosuspensions, nanocrystals, nanotubes and nanowires, functionalized nanocarriers, nanospheres, nanocapsules, liposomes, lipid emulsions, lipid microtubules/microcylinders, lipid microbubbles, liposheres, lipopolyplexes, inverse lipid micelles, dendrimers, ethosomes, multicomposite ultrathin capsules, aquasomes, pharmacosomes, colloidosomes, niosomes, discomes, proniosomes, microspheres, microemulsions and polymeric micelles. Other suitable pharmaceutically acceptable excipients are inter alia described in Remington's Pharmaceutical Sciences, 15th Ed., Mack Publishing Co., New Jersey (1991) and Bauer et al., Pharmazeutische Technologie, 5th Ed., Govi-Verlag Frankfurt (1997). The person skilled in the art will readily be able to choose suitable pharmaceutically acceptable carriers, depending, e.g., on the formulation and administration route of the pharmaceutical composition.

In a further embodiment the vaccine composition comprises one or more viral or non-viral polypeptides, one or more viral or non-viral nucleic acid sequences and/or vaccine adjuvants, wherein said one or more viral polypeptides or said one or more viral nucleic acid sequences are not from the same virus as the HVLP or EBVLP in said vaccine composition.

The term "adjuvant" as used herein refers to a substance that enhances, augments or potentiates the host's immune response (antibody and/or cell-mediated) to an antigen or fragment thereof. Exemplary adjuvants for use in accordance with the present invention include inorganic compounds such as alum, aluminum hydroxide, aluminum phosphate, calcium phosphate hydroxide, the TLR9 agonist CpG oligodeoxynucleotide, the TLR4 agonist monophosphoryl lipid (MPL), the TLR4 agonist glucopyranosyl lipid (GLA), the water in oil emulsions Montanide ISA 51 and 720, mineral oils, such as paraffin oil, virosomes, bacterial products, such as killed bacteria *Bordetella pertussis, Mycobacterium bovis*, toxoids, nonbacterial organics, such as squalene, thimerosal, detergents (Quil A), cytokines, such as IL-1, IL-2, IL-10 and IL-12, and complex compositions such as Freund's complete adjuvant, and Freund's incomplete adjuvant. Generally, the adjuvant used in accordance with the present invention preferably potentiates the immune response to the multimeric complex of the invention and/or modulates it towards the desired immune responses.

The term "pharmaceutically acceptable" means a non-toxic material that does not interfere with the effectiveness of the biological activity of the multimeric complex according to the present invention.

In a further embodiment the present invention relates to the use of the HVLP or the EBVLP as described herein or the composition comprising the HVLP or the EBVLP as described herein, or the vaccine composition comprising the HVLP or the EBVLP as described herein in the vaccination or treatment of a subject.

The amount necessary and the treatment regimen for an effective immunization may vary and depend on such factors as the individual's size, body surface area, age, sex, time and route of administration, general health, and other drugs being administered concurrently. Said effective amount is expected to be in broad range and can for any given situation be readily determined by routine experimentation and is within the skills and judgement of the ordinary clinician or physician. The mode of administration can be any mode of administration that results in the immunization of the individual exposed to the vaccine for immunization and includes parenteral administration such as, e.g., intravenous, intramuscular, intraperitoneal, intrasternal, subcutaneous, intraarticular injection or infusion and inhalation, as well as enteral administration. Preferably, the vaccine is administered at least 2 times in order to maximize the effect of the immunization.

The term "vaccination" as used herein relates to the administration of antigenic material to a subject in order to stimulate the immune system of the subject in order to prophylactically or therapeutically immunize the subject against a Herpes virus or EBV infection or diseases associated with the viruses. According to the invention, prophylactic immunization refers to the first exposure of an individual's immune system, i.e. a naïve immune system, to Herpes virus or EBV antigens. Said first exposure results in the clearance of said antigens from the body of the exposed individual and in the development of Herpes virus- or EBV-antigen specific CD4+ and CD8+ T-cells and antibody-producing memory B-cells. Upon a second exposure the immune system is able to prevent Herpes virus or EBV infection and/or clear said infection more effectively thereby preventing or mitigating the development of Herpes virus- or EBV-associated diseases. Specifically, the effects of said prophylactic immunization manifest itself in at least one of the following: preventing infection of the immunized individual with the Herpes virus or EBV, modifying or limiting the infection, aiding, improving, enhancing or stimulating the recovery of said individual from infection and generating immunological memory that will prevent or limit a subsequent Herpes virus or EBV infection. The presence of any of said effects can be tested for and detected by routine methods known to the person skilled in the art. Preferably, the patient is challenged with one or more Herpes virus or EBV antigens which have been part of the vaccine used and antibody titers and the number of T-cells against said one or more antigens are determined. Also, the induction of neutralizing antibodies that inhibit infection of human B-cells in vitro can be determined. While equally provoking an immune response against Herpes virus or EBV antigens, therapeutic immunization in accordance with the present invention is performed on individuals that have been exposed to the Herpes virus or EBV prior to said immunization, i.e. they are already infected with the Herpes virus or EBV. In this case, immunization leads to the reactivation of resting T effector cells, which are confronted with the cognate antigens in a form that these antigens are presented by professional antigen-presenting cells in association with MHC class I and/or MHC class II molecules. Therapeutic immunization against EBV may prove particularly relevant in cases where the reactivation of the virus is undesirable such as, e.g. in transplant recipients or otherwise immuno-compromised patients (HIV-positive individuals, cancer patients, patients with severe inflammatory or autoimmune diseases), or in cases where EBV-reactivation can lead to or has led to the development of a disease like posttransplant lymphoproliferative disorders (PTLD) and Non-Hodgkin lymphoma, chronic active EBV infection (CAEBV), oral hairy leukoplakia or in cases where the B-cell transforming capacity of EBV has led to the development of a disease such as, e.g. cancer.

In a further embodiment the present invention relates to the use of the nucleic acid molecule encoding the Herpes viral proteins of the HVLP or the EBV proteins of the EBVLP, the vector comprising said nucleic acid molecule, the composition of matter comprising at least two nucleic acid molecules encoding the Herpes viral proteins of the HVLP or the EBV proteins of the EBVLP, wherein the at least two nucleic acid molecules are preferably comprised by at least two vectors, the host cell transfected with said nucleic acid molecule, said vector or said composition in the production of a HVLP or an EBVLP.

The present invention further pertains to a kit comprising the HVLP as described herein, the EBVLP as described herein, the nucleic acid molecule encoding the Herpes viral proteins of the HVLP or the EBV proteins of the EBVLP, the vector comprising said nucleic acid molecule, the composition of matter comprising at least two nucleic acid molecules encoding the Herpes viral proteins of the HVLP or the EBV proteins of the EBVLP, wherein the at least two nucleic acid molecules are preferably comprised by at least two vectors, the host cell transfected with said nucleic acid molecule, said vector or said composition, the composition comprising at least 95% of the HVLP or the EBVLP as described herein and/or the vaccine composition as described herein.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having". When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

The term "about" or "approximately" as used herein means within 20%, preferably within 10%, and more preferably within 5% of a given value or range. It includes also the concrete number, e.g., about 20 includes 20.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well-known in the art. Generally, nomenclatures used in connection with techniques of biochemistry, enzymology, molecular and cellular biology, microbiology, genetics and protein and nucleic acid chemistry and hybridization described herein are those well-known and commonly used in the art.

The methods and techniques of the present invention are generally performed according to conventional methods well-known in the art and as described in various general and more specific references that are cited and discussed throughout the present specification unless otherwise indicated. See, e. g., Sambrook et al., Molecular Cloning: A Laboratory Manual, 3rd ed., Cold Spring Harbor Laboratory Press, Cold Spring Harbor, N. Y. (2001); Ausubel et al., Current Protocols in Molecular Biology, J, Greene Publishing Associates (1992, and Supplements to 2002); Handbook of Biochemistry: Section A Proteins, Vol 1 1976 CRC Press; Handbook of Biochemistry: Section A Proteins, Vol II 1976 CRC Press. The nomenclatures used in connection with, and the laboratory procedures and techniques of, molecular and cellular biology, protein biochemistry, enzymology and medicinal and pharmaceutical chemistry described herein are those well-known and commonly used in the art.

FIGURES

FIG. 1: EBV miRNAs affect major pathways of immunity. (A) Heatmaps of the most strongly regulated genes in wt/B95-8 or ΔmiR EBV-infected B-cells of 6 donors (donor Ad1-Ad6) five days post infection. Differentially expressed gene transcripts with absolute z-scores>1.6 are shown. Negative and positive log 2 fold change values indicate down- and up-regulated transcripts, respectively, in wt/B95-8 compared with ΔmiR EBV-infected cells. (B) Regulation of selected genes associated with adaptive immune responses or the p53 signaling pathway. Previously reported targets of EBV miRNAs and common housekeeping genes are shown as well. Negative log 2 fold change values indicate genes down-regulated by viral miRNAs. (C) The fractions of EBV miRNAs among all miRNAs. Means of 6 donors is shown.

FIG. 2: EBV miRNAs inhibit secretion of pro-inflammatory cytokines and expression of molecules involved in antigen processing and presentation. (A) Secretion of various cytokines by B-cells infected with wt/B95-8 or ΔmiR EBV. B-cells, which had been infected 4 or 11 earlier (days post infection, dpi), were cultivated for 4 additional days to determine cytokines levels by ELISA (n=3). CpG DNA was added as indicated. (B) EBV miRNAs regulate IL12B and TAP2. HEK293T cells were co-transfected with miRNA expression vectors and luciferase reporter plasmids carrying a wild type or mutated 3'-UTR (FIG. 7) as indicated (n=3). The luciferase activities were normalized to lysates from cells co-transfected with the wild type 3'-UTR reporter and an empty plasmid. wt: wild type 3'-UTR, mut: mutated 3'-UTR, ø: empty plasmid. P values were calculated by an unpaired two-tailed T test. An asterisk (*) indicates p<0.05 with respect to the luciferase activity of the wild type reporter co-transfected with empty plasmid. (C) Western blot analysis of TAP1 and TAP2 in EBV-infected B-cells. Tubulin (TUBB) and β-Actin (ACTB) serve as housekeeping controls. A positive control is IPO7. Representative examples (top) and protein expressions normalized to tubulin (bottom; n=3-5) are shown. (D-E) Cell surface expression of HLA molecules (D) and co-stimulatory and adhesion molecules (E) regulated by EBV miRNAs. Median fluorescence intensity (MFI) was measured after immunostainings for individual surface proteins and ratios (wt/B95-8 divided by ΔmiR EBV-infected B-cells) are shown (n=5-10). Means±SD are shown. n.d.: not detected; wt: wt/B95-8; *: p<0.05, : p<0.01, *: p<0.001.

FIG. 3: EBV miRNAs prevent Th1 differentiation and recognition by EBV-specific CD4$^+$ T-cells. (A) Schematic overview of co-culture experiments to assess the impact of viral miRNAs on helper T-cell differentiation. (B) Th1 differentiation of naive CD4$^+$ T-cells upon co-culture with EBV-infected B-cells. Naive CD4$^+$ T-cells were cultivated for 7 days with autologous, newly infected B-cells and αCD3/αCD28 antibodies at indicated ratios (n=5-6). Proliferating, phorbol 12-myristate 13-acetate (PMA) and ionomycin re-stimulated Th1 cells were quantitated by intracellular IFN-γ staining. Left: representative flow cytometry analyses; right: summary of all experiments. (C) An anti-IL12B antibody (5 µg/ml) suppressed Th1 cell differentiation of naive CD4$^+$ T-cells co-cultivated with wt/B95-8 or ΔmiR-infected B-cells at B:T-cell ratio of 1:1 (n=8). An irrelevant antibody of the same isotype was used as a control. (D) Schematic overview of co-culture experiments investigating the influence of viral miRNAs on antiviral functions of EBV-specific CD4+ T-cells. (E) IFN-γ release by polyclonal EBV-specific CD4+ T-cells co-cultured with autologous (auto), HLA-matched, or mismatched (mis.) B-cells infected with EBV (n=3; FIG. 12). The B:T-cell ratio was 1:1. Matched HLA class II alleles are indicated. ø: only T-cells; n.a.: not applicable. (F) Cytotoxic activity of EBV-specific CD4+ T-cells. Killing of EBV-infected B-cells was analyzed at various B:T-cell ratios by Calcein release assays. A representative experiment with HLA-matched EBV-infected target B-cells (left; n=3) and the overview of all experiments with HLA-matched B-cells (right) are described. Means±SD are shown. *: p<0.05, : p<0.01, *: p<0.001.

Figure 4:
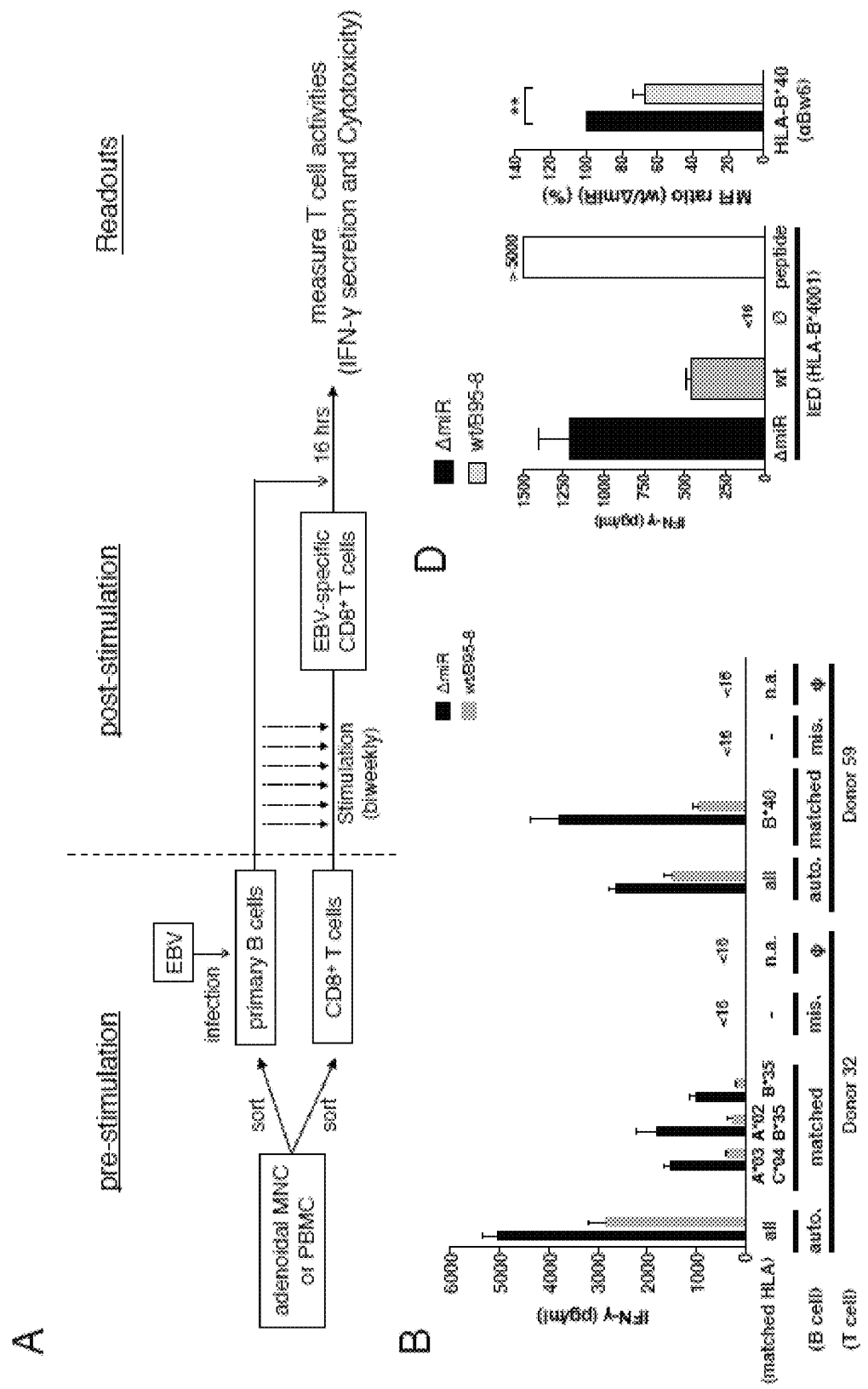
Figure 4:
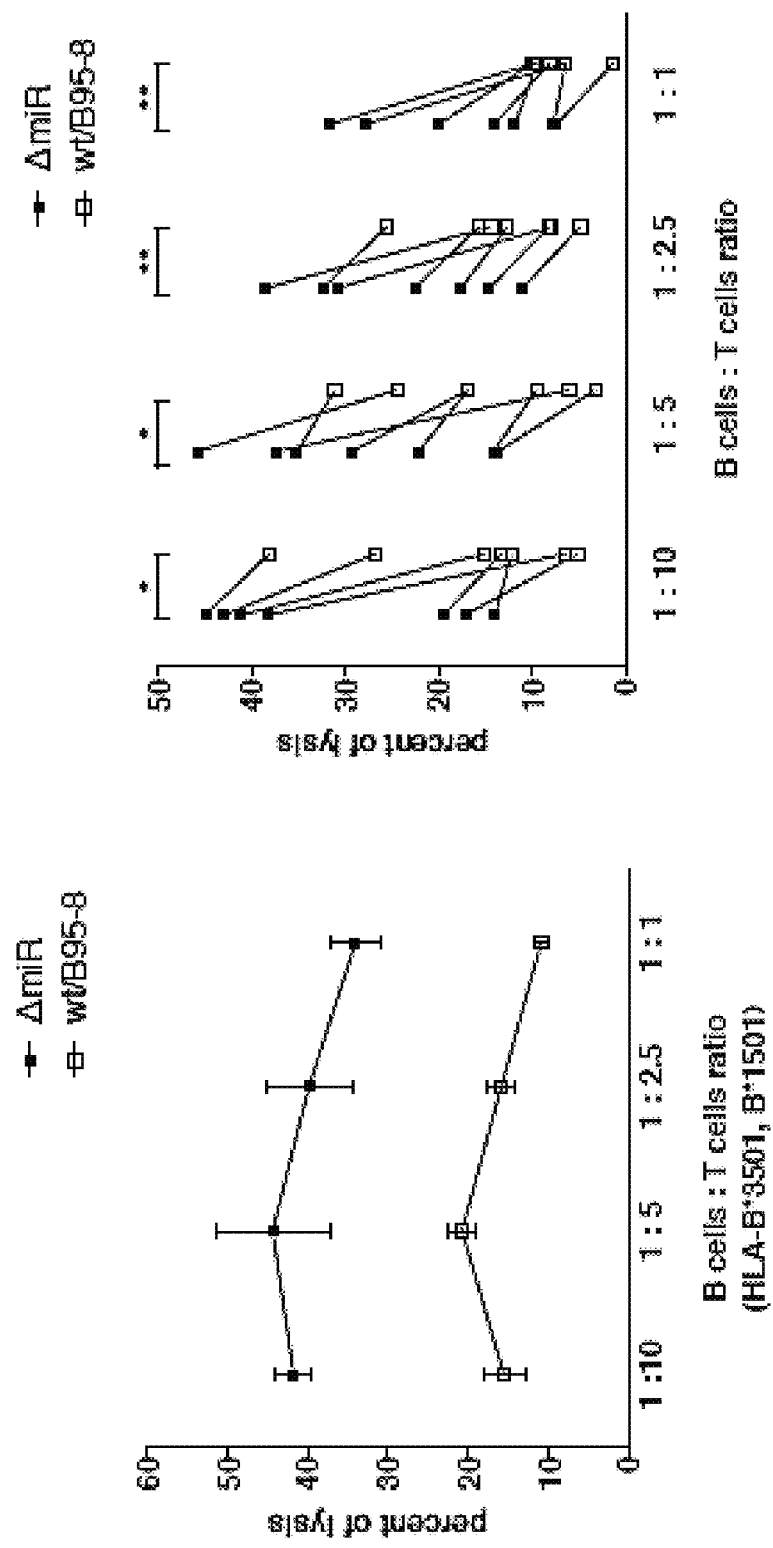

FIG. 4: EBV miRNAs inhibit recognition of EBV-infected B-cells by EBV-specific CD8+ T-cells. (A) Schematic overview of co-culture experiments investigating the influence of viral miRNAs on antiviral functions of EBV-specific CD8+ T-cells. (B) IFN-γ release by polyclonal EBV-specific CD8+ T-cells co-cultured with autologous (auto), HLA-matched, or mismatched (mis.) B-cells infected with EBV (n=3; FIG. 12). The B:T-cell ratio was 1:1. Matched HLA class I alleles are indicated. ø: only T-cells; n.a.: not applicable. (C) Cytotoxic activity of EBV-specific CD8+ T-cells. Killing of EBV-infected B-cells (wt/B95-8 or ΔmiR EBV) was analyzed at various B:T-cell ratios in calcein release assays. A representative experiment with HLA-matched EBV-infected target B-cells (left; n=3) and the overview of all experiments with HLA-matched B-cells (right) are shown. (D) Reactivity of a CD8+ T-cell clone directed against a LMP2 epitope IED (HLA-B*40:01-restricted). T-cells were cultivated for 16 hours with HLA-B*40:01-positive B-cells that have been infected for 15 days. IFN-γ secretion levels quantified with ELISA (Left; n=3) and MFI ratios (wt/B95-8 divided by ΔmiR EBV-infected B-cells) for HLA-B*40 (Right; n=4) are described. ø: only T-cells; peptide: T-cells loaded with the control peptide. wt: wt/B95-8. Means±SD are shown. *: p<0.05, **: p<0.01.

Figure 5:
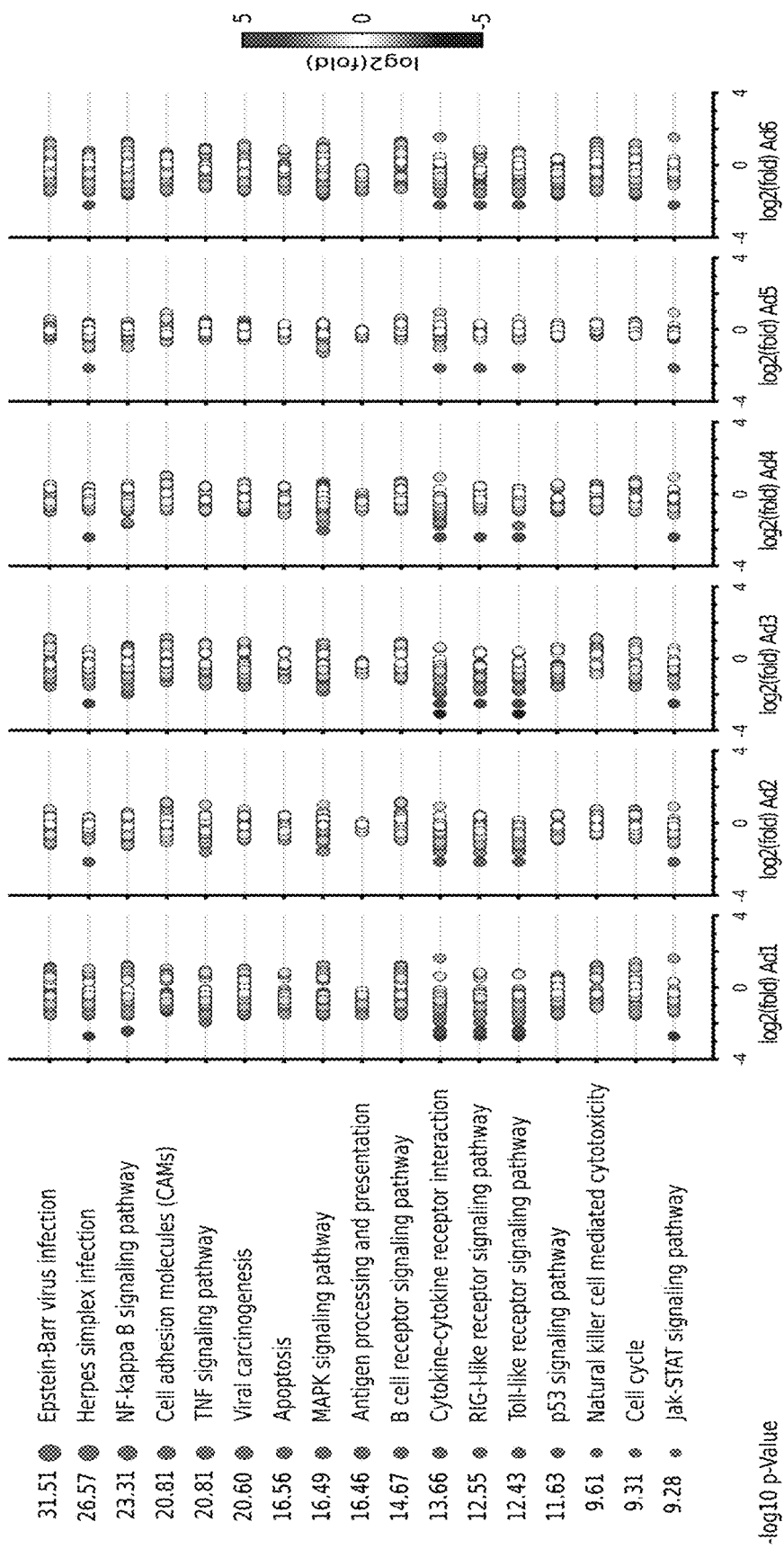

FIG. 5: The regulation of functional gene groups by EBV miRNAs KEGG pathway categories were used for categorization of gene functions. Pathways are sorted by statistical significance. The sizes of the dots indicate −log 10 p-value scores. For each of the six donors, fold change values of differentially expressed transcripts are plotted. As in FIG. 1a, negative and positive $\log_2$ fold change values indicate down- or up-regulation by EBV miRNAs, respectively.

Figure 6:
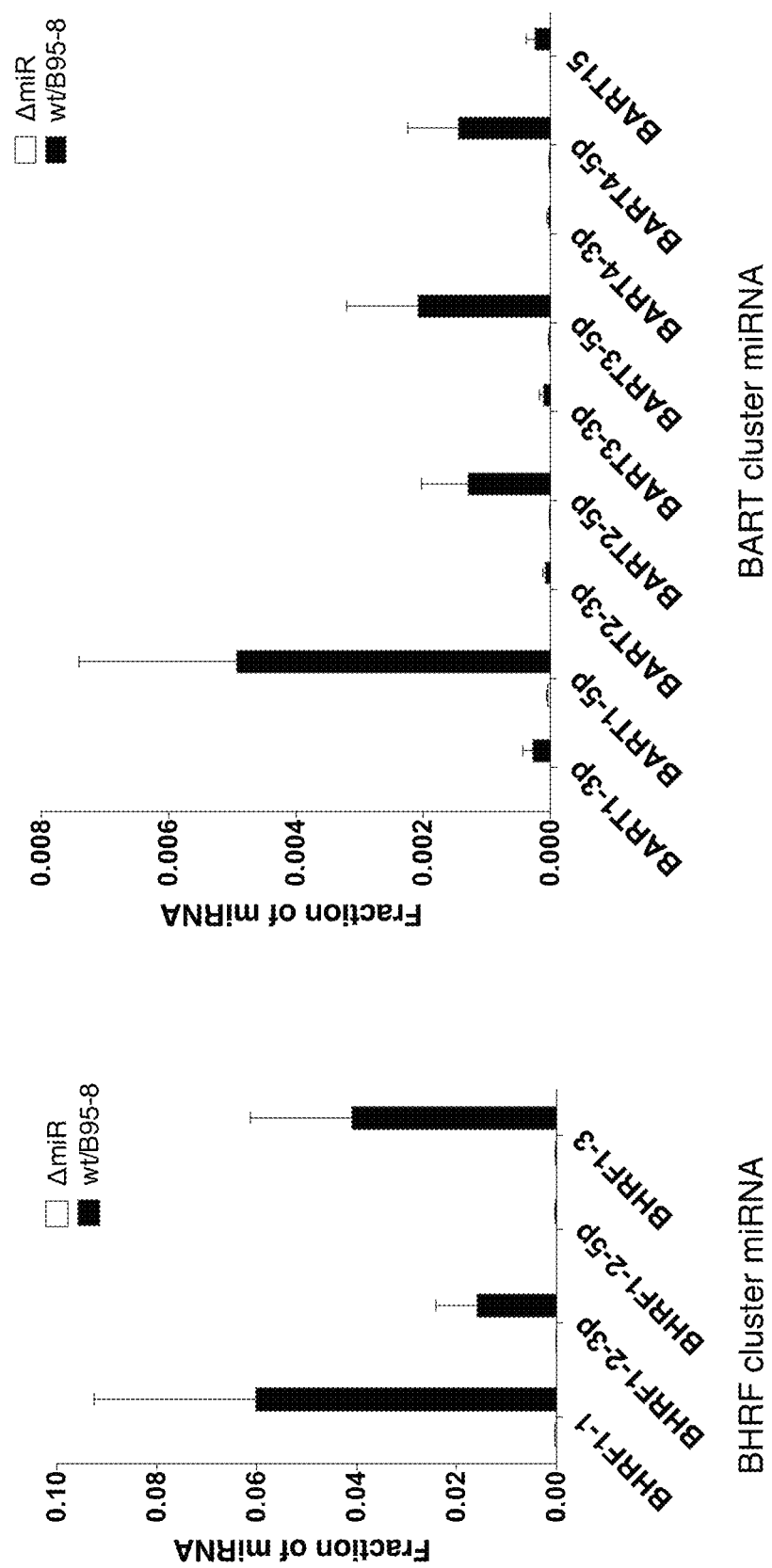

FIG. 6: Quantification of EBV miRNAs after RISC-IP EBV's BHRF and BART miRNAs accumulate in wt/B95-8 EBV-infected B-cells but are barely detectable in ΔmiR EBV-infected B-cells. Means±SD is shown.

FIG. 7: 3'-UTR reporters and their mutations Partial sequences of 3'-UTRs of selected transcripts (IL12B target sequences BART2; SEQ ID NOs: 2 and 4; IL12B target sequences BART10; SEQ ID NOs: 7 and 9; IL12B target sequence BART22; SEQ ID NO: 12; TAP2 target sequence BHRF1-3; SEQ ID NO: 15; IL12B target sequence BART1; SEQ ID NO: 18; and TAP2 target sequences BART17; SEQ ID NOs: 21 and 23), which were analyzed in FIG. 2b are shown together with corresponding miRNAs (BART2 miRNA; SEQ ID NO: 1; BART10 miRNA; SEQ ID No: 6, BART22 miRNA; SEQ ID NO: 11; BHRF1-3 miRNA; SEQ ID NO: 14; BART1 miRNA; SEQ ID NO: 17; and BART17 miRNA; SEQ ID NO. 20) and mutations (mutated IL12B target sequences BART2; SEQ ID NOs: 3 and 5; mutated IL12B target sequences BART10; SEQ ID NOs: 8 and 10; mutated IL12B target sequence BART22; SEQ ID No: 13; mutated TAP2 target sequence BHRF1-3; SEQ ID NO: 16; mutated IL12B target sequence BART1; SEQ ID NO: 19; and mutated TAP2 target sequences BART17; SEQ ID NOs: 22 and 24) within the 3'-UTRs in reporter vectors. Complementarities are based on in silico predictions according to the RNAhybrid algorithm and depicted as Watson-Click ('|') or G:U (':'). Non-matching nucleotide residues are indicated (X). They result from mutated mRNA target sequences in the reporter plasmids.

Figure 8:
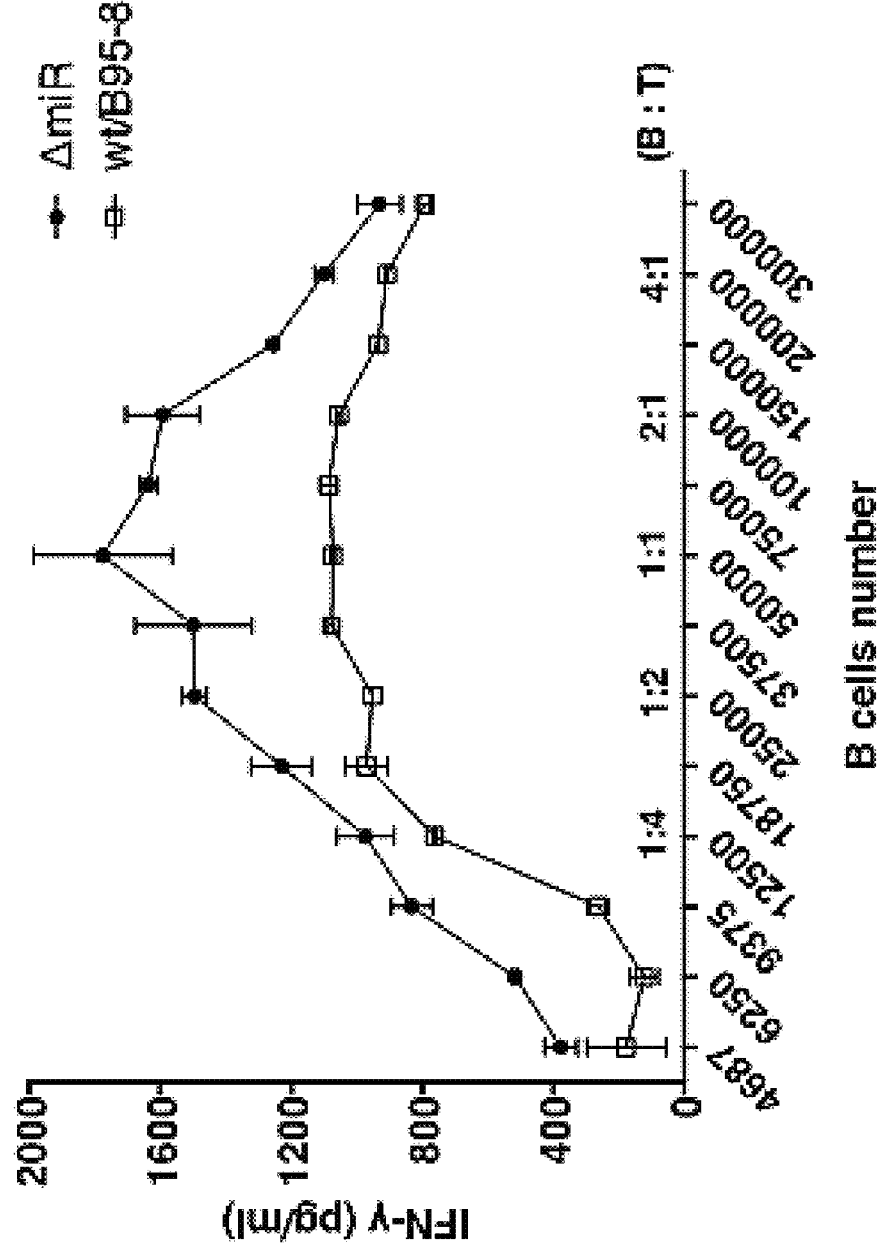

FIG. 8: Reactivity of polyclonal EBV-specific CD4+ T-cells

EBV-specific CD4+ T-cell were co-cultured for 16 hours with autologous B-cells that had been infected five days earlier. IFN-γ secretion levels were then quantified with ELISA. Various B:T-cell ratios were used as indicated.

Figure 9:
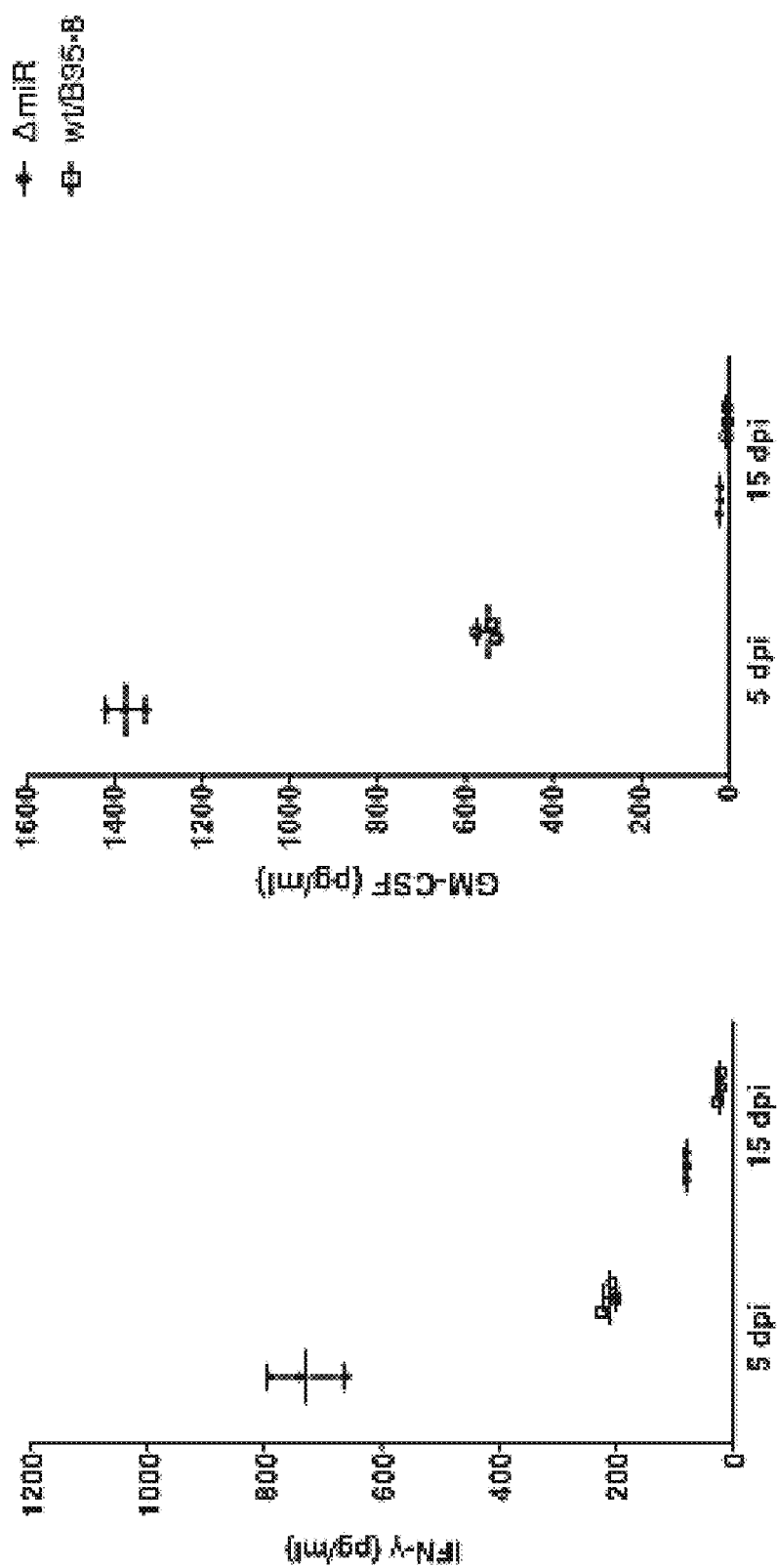

FIG. 9: Reactivity of the gp350 specific CD4+ T-cell clone

The gp350-specific CD4+ T-cell clone, epitope FGQ (HLA-DRB1*1301), was used as effector cells. Autologous B-cells from donor JM (table S2) were used as target cells five and 15 days after infection with the two EBV strains indicated at an B:T-cell ratio of 1:1. After 16 hours of co-culture, IFN-γ and GM-CSF secretion levels were quantified by ELISA. Means±SD are shown.

Figure 10:
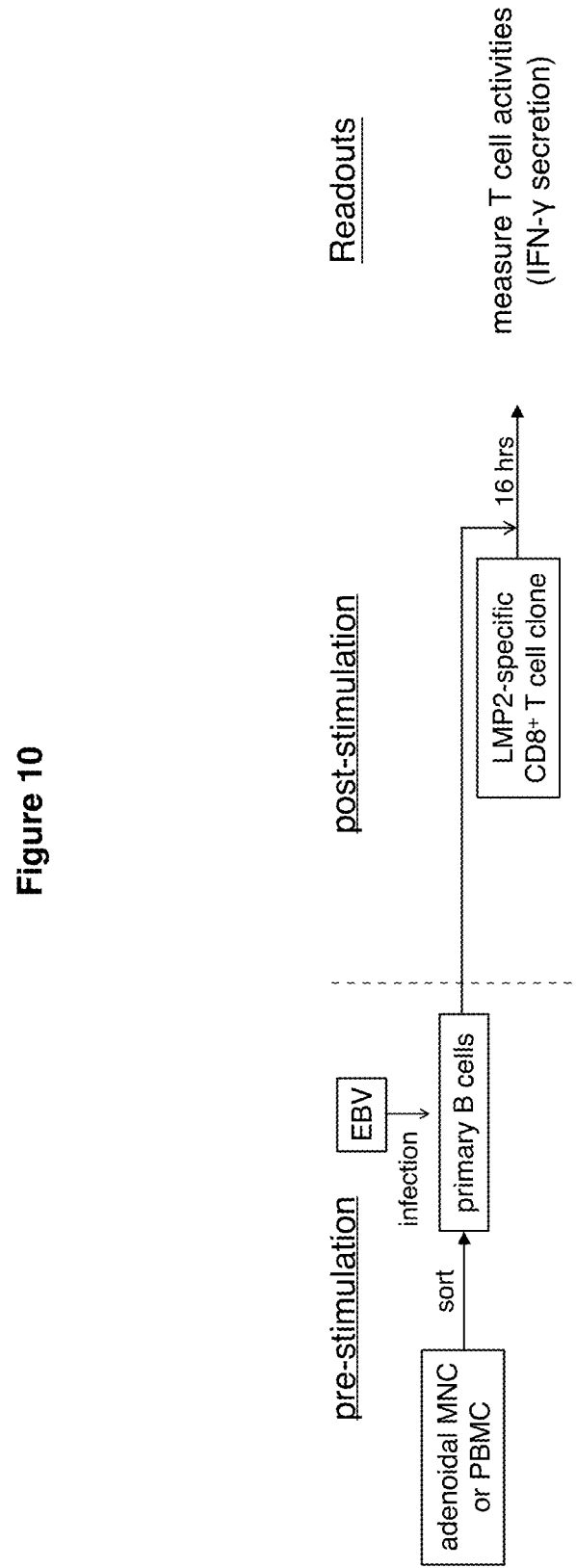

FIG. 10: Schematic overview of co-culture experiments investigating the influence of viral miRNAs on antigen presentation to a LMP2-specific CD8+ T-cells clone FIG. 11: Regulation of viral genes by EBV miRNAs (A) Western blot analysis of LMP2A expression in B-cells infected with wt/B95-8 or with ΔmiR EBV at day 15 post infection. A representative example (top) and protein expression normalized to tubulin (bottom n=4) are described. Means±SD are shown. (B) Loge fold changes of two LMP2 gene variants by viral miRNAs. Analysis was performed as in FIG. 1B but the quantification of expression level was done exon-wise to analyse splicing variants correctly.

FIG. 12: HLA alleles.

List of the donors' HLA alleles (MVZ Martinsried, Germany) identified by deep-sequencing, whose B and T-cells have been used in co-culture experiments in this study. n.a.: not available.

FIG. 13: Activation of CD4+ T-cells using Epstein-Barr VLPs A human EBV-immortalized B-cell line (LCL) was incubated with similar numbers of VLPs (1*10^4 particles/cell) with miRNAs or lacking all miRNAs (ΔmiRNAs) for 24 hours and then co-cultivated for another 24 hours with an HLA-matched CD4+ T-cell clone specific for the EBV tegument protein BNRF1 for another 24 h. Activation of T cells was quantified in an IFNγ-ELISA assay. Controls are LCLs or T-cells that have not been co-cultivated with LCLs (T-cells only).

EXAMPLES

The following Examples illustrate the invention, but are not to be construed as limiting the scope of the invention.

Materials and Methods

Separation of Human Primary Cells

Human primary B and T-cells were prepared from adenoidal mononuclear cells (MNC) or peripheral blood mononuclear cells (PBMC) by Ficoll-Hypaque gradient centrifugation. B-cells, CD4+ T-cells, CD8+ T-cells, and naive CD4+ T-cells were separated from adenoidal MNC or PBMC using MACS separator (Miltenyi Biotec) with CD19 MicroBeads, CD4 MicroBeads, CD8 MicroBeads, and Naive CD4+ T-cell Isolation Kit II, respectively.

Cell Lines and Cell Culture

The EBV-positive Burkitt's lymphoma cell line Raji and HEK293-based EBV producer cell lines (Seto et al., *PLoS Pathog.* 6, e1001063 (2010)), infected human primary B-cells, and isolated T-cells were maintained in RPMI 1640 medium (Life Technologies). HEK293T cells were maintained in DMEM medium. All media were supplemented with 10% FBS (Life Technologies), penicillin (100 U/ml; Life Technologies), and streptomycin (100 mg/ml; Life Technologies). Cells were cultivated at 37° C. in a 5% $CO_2$ incubator.

Preparation of Infectious EBV Stocks and Infection of Human Primary B-Cells

Infectious EBV stocks were prepared as described (Seto, loc. cit.). Briefly, EBV producer cell lines for ΔmiR (4027) and wt/B95-8 (2089) EBV strains were transiently transfected with expression plasmids encoding BZLF1 and BALF4 to induce EBV's lytic phase. Supernatants were collected three days after transfection and debris was cleared by centrifugation at 3000 rpm for 15 minutes. Virus stocks were titered on Raji cells as previously reported (Seto, loc. cit.). For virus infection, primary B-cells were cultivated with each virus stock for 18 hours. After replacement with fresh medium, the infected cells were seeded at an initial density of $5 \times 10^5$ cells per ml.

RNA-Seq and RISC-IP

At 5 days post infection of human primary B-cells, total RNAs were extracted with Trizol (Life Technologies) and Direct-Zol RNA MiniPrep (Zymo Research) from six different donors (Ad1 to Ad6) (FIG. 1) for RNA-Seq, according to the manufacturers' protocols. In parallel, RISC immunoprecipitation (RISC-IP) was performed as described previously (Kuzembayeva, et al., *PLoS ONE.* 7, e47409 (2012)). Briefly, lysed cells were incubated with anti-Ago2 antibody (11A9)-conjugated dynabeads (Life Technologies), washed, and co-precipitated RNA was extracted. The cDNA libraries were prepared (vertis Biotechnologie AG, Freising, Germany). For RNA-Seq, total RNAs were depleted of rRNAs by Ribo-Zero rRNA Removal Kit (Illumina), fragmented by ultrasonication, and subjected to first strand synthesis with a randomized primer. For RISC-IP, RNAs were poly (A)-tailed, ligated with an RNA adapter at 5'-phosphates to facilitate Illumina TruSeq sequencing, and subjected to first strand synthesis with a oligo-(dT) primer. The cDNAs were PCR-amplified and sequenced with an Illumina HiSeq2000 instrument at the University of Wisconsin Biotechnology Center DNA Sequencing Facility.

Analysis of Deep Sequencing

For RNA-Seq, processing of paired-end reads (poly-A tail filtering, N-filtering, adapter removal) was done using FastQC and R2M (RawReadManipulator). Reads were mapped to the human genome (hg19 'core' chromosome-set) by STAR and feature counts per transcript were determined using featureCounts and GencodeCV19 annotations together with EBV's annotation (GenBank: AJ507799). To screen differentially regulated genes by viral miRNAs, it was used a simple but efficient scoring algorithm based on donor/replicate wise fold changes ranks. For each gene g and replicate k it is calculated the gene specific rank score:

$$r_g = \frac{1}{m} \sum_{k=1}^{n} r_{gk}$$

where n is the number of all replicates, m the number of all genes/transcripts, $r_{gk}$ the rank of gene g in sample k.

To select highly differentially expressed genes the rank score was transformed into a z-score and selected all transcripts with an absolute z-score>1.6.

For RISC-IP the mapped reads were normalized using size factors estimated with the R package DEseq2 and filtered for reads mapped to annotated 3'UTR regions using Gencode v19. To identify local quantitative differences in the read enrichments on 3'UTRs between wt EBV compared with ΔmiR EBV-infected B cells, a donor-wise relative enrichment score was calculated. For each genomic position p, the relative expression $es_p$ was calculated as:

$$es_p = \frac{e_{tp}}{e_{tp} + e_{cp}} \cdot n_{pu}$$

where $e_{tp}$ is the expression value at position p in wt EBV-infected cells and $e_{cp}$ the local expression value in ΔmiR EBV-infected B cells, respectively.

The normalization factor $n_{pu} = e_{tp}/\max(e_u)$ was introduced to correct for local maxima in the UTR sequence of interest, where $\max(e_u)$ is the maximum expression value in the UTR sequence u. Finally a Gaussian filter was used to minimize local noise. To select 3'-UTRs bound by viral miRNAs, the threshold was set as follows: enrichment score>0.6 for a stretch of >20 nucleotides in the 3'-UTRs in two or more donors.

KEGG Enrichment Pathway

Enrichment of specific pathways was estimated by performing a hypergeometric distribution test via the KEGG API Web Service. All calculations were done using Matlab (Mathworks).

ELISA

To detect cytokine secretion from infected B-cells, $1 \times 10^6$ cells were seeded in 6 well plates at four or 11 days post infection, cultivated for four days with cyclosporine (1 µg/ml; Novartis). Supernatants were harvested and stored at −20° C. Enzyme-linked immunosorbent assays (ELISAs) for interleukin-6 (IL-6), IL-10, IL12B (IL-12p40), IL-12, IL-23, and TNF-α were performed following the manufacturer's protocols (Mabtech). For IL-6, IL-10, and TNF-α, CpG DNA were added as previously described (Iskra, et al., *J. Virol.* 84, 3612-3623 (2010)) to stimulate infected B-cells. ELISA for IFN-γ levels was performed following the manufacturer's protocol (Mabtech).

Flow Cytometry and Antibodies

After immunostainings with fluorophore-conjugated antibodies, single-cell suspensions were measured with LSR-Fortessa or FACSCanto (BD) flow cytometers and the FACSDiva software (BD Biosciences). Acquired data were analyzed with FlowJo software Ver. 9.8 (FlowJo). The following fluorophore-conjugated antibodies reactive to human antigens were used: anti-human IFN-γ APC (4S.B3, IgG1; Biolegend), anti-CD40 PE (5c3, IgG2b; BioLegend), anti-ICOS-L (B7-H2) PE (2D3, IgG2b; BioLegend), anti-PD-L1 (B7-H1) APC (29E.2A3, IgG2b; BioLegend), anti-CD86 (B7-2) PE (37301, IgG1; R&D Systems), anti-CD54 (ICAM-1) APC (HCD54, IgG1; BioLegend), anti-HLA-ABC APC (W6/32, IgG2a; BioLegend), anti-CD80 PE-Cy5 (L307.4; BD Pharmingen), anti-FAS (CD45) PE (Dx2, IgG1; BioLegend), anti-HLA-DR unlabeled (L234, IgG2a; BioLegend), anti-HLA-DQ unlabeled (SPV-L3, IgG2a; AbD Serotec), anti-HLA-DP unlabeled (B7/21, IgG3; Abcam), anti-mouse F(ab')2 APC (polyclonal, IgG; eBioscience), HLA-Bw6 PE (REA143, IgG1; Miltenyi Biotec), isotype IgG1 PE (MOPC-21; BioLegend), isotype IgG2b PE (MPC-11; BioLegend), isotype IgG1 APC (MOPC-21; BD Bioscience), isotype IgG2a APC (MOPC-173; BioLegend), isotype IgG2b APC (MG2b-57; BioLegend).

Western Blotting

Cells were lysed with RIPA buffer (50 mM Tris-HCl (pH 8), 150 mM NaCl, 0.1% SDS, 1% NP-40, 0.5% DOC) and boiled the extracts with Laemmli buffer. Proteins were separated on 10% SDS-PAGE gels (Carl Roth) and transferred to nitrocellulose membranes (GE Healthcare Life Science) using Mini-PROTEAN Tetra Cell (Bio-Rad). Membranes were blocked for 30 minutes with Roti-Block (Carl Roth) followed by antibody incubation. Secondary antibodies conjugated with horseradish peroxidase were used (Cell Signaling) and exposed to CEA films (Agfa HealthCare). Protein levels were quantified with the software ImageJ. The following primary antibodies reactive to human proteins were used: anti-human Tubulin (B-5-1-2; Santa Cruz), anti-human actin (AC-74; Sigma), anti-human IP07 (ab88339; Abcam), anti-human TAP1 (1.28; Acris) and anti-human TAP2 (2.17, Acris). The (TP-1467) monoclonal antibody reactive to the EBV protein LMP2 was provided by Elisabeth Kremmer.

Luciferase Reporter Assays

The 3'-UTRs of IL12B (Ensembl: ENST00000231228) and TAP2 (Ensembl: ENST00000374897) were cloned downstream of firefly luciferase (Fluc) in the expression plasmid psiCHECK-2 (Promega). To construct the viral miRNA expression vectors, TagBFP (Evrogen) was cloned under the control of the EF1α promoter into pCDH-EF1-MCS (System Biosciences). Single miRNAs of interest were cloned downstream of the TagBFP-encoding gene. Viral miRNAs were obtained by PCR from the p4080 plasmid (Seto, loc. cit.). The psiCHECK-2 reporter and pCDH-EF1 miRNA expressor plasmid DNAs were co-transfected into HEK293T cells by Metafectene Pro (Biontex). After 24 hours of transfection, luciferase activities were measured with the Dual-Luciferase Assay Kit (Promega) and the Orion II Microplate Luminometer (Titertek-Berthold). The activity of Fluc was normalized to the activity of Renilla luciferase (Rluc) encoded in the psiCHECK-2 reporter. It was performed in silico prediction of EBV miRNA binding sites on 3'-UTRs primarily with TargetScan (world wide web targetscan.org) and employed RNAhybrid (world wide web bibiserv.techfak.uni-bielefeld.de/rnahybrid) to screen for 6mer binding sites (Bartel, *Cell*. 136, 215-233 (2009)). Site-directed mutagenesis were performed with overlapping oligo DNAs and Phusion polymerase (NEB).

Establishment of EBV-Stimulated Effector T-Cells and T-Cell Clones

EBV-specific CD8+ T-cell clones were established from polyclonal T-cell lines that were generated by lymphoblastoid cell lines (LCLs) or mini-LCL stimulation of PBMCs as previously described (Adhikary et al. *PLoS ONE*. 2, e583 (2007))

T-Cell Differentiation and Recognition

Th1 differentiation was assessed by co-culture of sorted naive CD4+ T-cells and infected B-cells 5 days post infection. 1×10$^5$ naive CD4+ T-cells stained with CellTrace Violet (Life Technologies) and 0.5 or 1×10$^5$ infected B-cells were cultured in 96 well plates with Dynabeads Human T-Activator CD3/CD28 (Life Technologies) and cultivated for 7 days. The neutralizing antibody against IL12B (C8.6; BioLegend) or the corresponding isotype control antibody (MOPC-21; BioLegend) were added for certain experiments at 5 µg/ml. Cells were re-stimulated with PMA and ionomycin (Cell Stimulation Cocktail; eBioscience) for 5 hours and treated with Brefeldin A and Monensin (Biolegend) for 2.5 hours prior to fixation. Th1 population was measured by intracellular IFN-γ staining with FIX & PERM Cell Permeabilization Kit (Life Technologies) and subsequent flow cytometry analysis. The Th1 population was defined as IFN-γ positive T-cells in the fraction of proliferating T-cells identified via CellTrace Violet staining. EBV-specific effector T-cells' activities were measured with ELISA and Calcein release assays. For IFN-γ detection from T-cells, effector and target cells were seeded at 5×10$^4$ cell per ml (1:1 ratio) each and co-cultured for 16 hours in a 96-well plate (V bottom). IFN-γ levels were detected with ELISA. IFN-γ concentrations lower than 16 µg/ml were considered as not detected.

T-Cell Cytotoxicity Assays

Primary infected B-cells were purified by Ficoll-Hypaque gradient centrifugation, and 5×10$^5$ target cells were labeled with calcein at 0.5 µg/ml. After three washing steps with PBS, target and effector cells were co-cultured in a 96-well plate (V bottom) with different ratios in RPMI red phenol-free medium to reduce background signals. After four hours of co-culture, fluorescence intensity of the released calcein was measured by the Infinite F200 PRO fluorometer (Tecan). As controls, spontaneous calcein release of target cells cultivated without effector cells and cells lysed with 0.5% Triton-X100 were used to define the levels of no and fully lysed target cells, respectively.

Statistical Analysis

Prism 6.0 software (GraphPad) was used for the statistical analysis and two-tailed ratio T test was applied unless otherwise mentioned.

Example 1

Targets of EBV's miRNAs using an approach designed to detect cellular mRNAs the virus targets to foster its efficient infection were searched. Two stocks of EBV, a laboratory strain (wt/B95-8) that expresses 13 miRNAs and its deleted derivative (ΔmiR) that expresses none, were used to infect freshly isolated B-cells from six donors. RNAs were isolated on day 5 following infection and sequenced. Genes that were differentially expressed were identified with those having a z-score>1.6 shown in FIG. 1A. These genes included the viral miRNA targets LY75/DEC205 (Skalsky et al., *PLoS Pathog*. 8, e1002484 (2012)) and IPO7 (Dölken et al., *Cell Host Microbe*. 7, 324-334 (2010)). The identified, regulated genes were grouped according to the Kyoto Encyclopedia of Genes and Genomes (KEGG) pathway categories (FIG. 5) based on consistently down-regulated genes in wt/B95-8 EBV infected cells. This grouping was enriched in the pathways linked to apoptosis, cell cycle regulation, and p53 signaling (Seto et al., *PLoS Pathog*. 6, e1001063 (2010)). This grouping also strikingly revealed that in newly infected cells, EBV's miRNAs regulate a wide array of immune functions encompassing antigen processing, HLAs and co-stimulatory molecules, and cytokine-cytokine receptor interaction (FIG. 1B, FIG. 5). RNA-induced silencing complex (RISC-IP) was immunoprecipitated and found 14.5% (±2.4% SD) of all miRNAs were of viral origin in wt/B95-8 EBV-infected cells (FIG. 1C and FIG. 6). It was also found that different mRNAs were detected in the RISC differently among the cell samples as has been found in PAR-CLIP experiments (Skalsky, loc. cit.) (GEO: GSE41437). Therefore, the analyses were focused primarily on candidate mRNAs identified by their differential expression in all samples (FIG. 1A) and used RISC-IP results to confirm them.

Example 2

It was confirmed that EBV's miRNAs regulate cytokines central to immune functions. The supernatants from B-cells infected with the two strains of EBV were assayed for the levels of interleukin-6 (IL-6), IL-10, TNF-α, IL12B (IL-12p40), IL-12 (p35/p40), and IL-23 (p19/p40). CpG DNA was added, which stimulates TLR9, for the detection of IL-6 and TNF-α secreted from EBV-infected cells (Iskra, et al., *J. Virol.* 84, 3612-3623 (2010)). The wt/B95-8 EBV-infected B-cells secreted less IL-6, TNF-α, and IL-12p40 than B-cells infected with ΔmiR EBV. In contrast, release of the anti-inflammatory cytokine IL-10 appeared to be unaffected by viral miRNAs (FIG. 2A) consistent with the transcriptome analysis (FIG. 1B). Secretion of IL-12 (p35/p40) and IL-23 (p19/p40), both of which contain the IL-12p40 subunit (Szabo et al., *Annu. Rev. Immunol.* 21, 713-758 (2003)), was significantly reduced in wt/B95-8 EBV-infected cells compared with ΔmiR EBV-infected cells (FIG. 2A).

Example 3

It was found that EBV miRNAs directly regulate a cytokine-encoding gene IL12B, which encodes IL-12p40. The finding was verified with luciferase reporter assays. EBV's miR-BHRF1-2, miR-BART1, or miR-BART2 repressed the luciferase activity of the IL12B reporter (FIG. 2B). The predicted binding sites of miR-BART1 or miR-BART2 were mutated, which abrogated their ability to inhibit the IL12B reporter (FIG. 2B and FIG. 7) confirming the direct controls of viral miRNAs on this gene transcript. MiR-BART10 and miR-BART22 were analysed, which are present in field strains of EBV but not in wt/B95-8 EBV, similarly (FIG. 2B and FIG. 7). Mutations of their predicted target sites only partially relieved the inhibition by both miRNAs, suggesting the presence of additional binding sites for these miRNAs in the IL12B transcript. In summary, it was confirmed that cytokines are regulated by EBV miRNAs, and validated IL12B as a direct target of multiple viral miRNAs.

Example 4

Additionally, levels of proteins pivotal to antigen processing and presentation, including TAP1 and TAP2, whose transcript levels were reduced in wt/B95-8 compared with ΔmiR EBV-infected cells were quantified (FIG. 1B). Both TAP1 and TAP2 were decreased by EBV's miRNAs (FIG. 2C). They form a heterodimer, which mediates the cytoplasmic transport of antigenic peptides into the ER lumen, where they are loaded onto MHC class I molecules stabilizing them (Horst et al., *J. Immunol.* 182, 2313-2324 (2009)). MHC class I molecules and all three subclasses of MHC class II molecules (HLA-DR, HLA-DQ and HLA-DP) were reduced as were co-stimulatory and adhesion molecules by 15 days post infection (FIGS. 2, D and E).

Example 5

RISC-IP and in silico algorithms indicated that the 3'-UTR of TAP2 is targeted by EBV miRNAs. In luciferase reporter assays miR-BHRF1-3 repressed the TAP2 reporter (FIG. 2B). Mutations of the target motif abrogated repression of luciferase, indicating that TAP2 is a direct target of miR-BHRF1-3 (FIG. 2B and FIG. 7). Similarly, miR-BART17, which is encoded by field strains of EBV, directly targeted the 3'-UTR of the TAP2 transcript (FIG. 2B and FIG. 7). Therefore, EBV miRNAs down-regulate genes with pivotal functions in peptide antigen processing, transport and presentation early after infection.

Example 6

Viral miRNAs inhibit the secretion of IL-12 early after infection (FIGS. 1B and 2A). This inhibition blocked differentiation of type 1 helper T (Th1) cells, a process for which IL-12 is critical (Szabo, loc. cit.). Naive CD4+ T-cells were co-cultured with autologous EBV-infected B-cells (FIG. 3A). The wt/B95-8 EBV-infected B-cells repressed Th1 differentiation compared with ΔmiR EBV-infected cells (FIG. 3B). An antibody that neutralizes the functions of IL12B, but not an isotype control antibody, suppressed Th1 differentiation when the cells were co-cultured with ΔmiR EBV-infected cells (FIG. 3C), indicating that IL-12 secreted from EBV-infected or activated B-cells per se drives the generation of Th1 cells. Thus, EBV miRNAs suppress the release of IL-12 from infected cells, a function that can abrogate antiviral control by virus-specific Th1 cells.

Example 7

Further, inhibition of MHC class II, co-stimulatory, and adhesion molecules by EBV miRNAs (FIGS. 1B and 2D, E) impaired MHC class I l-mediated recognition of infected cells by CD4+ T-cells. CD4+ T-cells were expanded ex vivo by repeated stimulation with an irradiated wt/B95-8 EBV-infected autologous lymphoblastoid cell line (LCL). The EBV-specific CD4+ T-cells were then co-cultured with autologous B-cells that had been infected with the two EBV strains 5 days earlier (FIG. 3D). Release of IFN-γ by EBV-specific CD4+ T-cells was substantial when co-cultured with ΔmiR EBV-infected cells as targets but was consistently reduced when co-cultured with wt/B95-8 EBV-infected B-cells at all cell ratios tested (FIG. 8). This effect was observed in autologous and HLA-matched but not in HLA-mismatched situations (FIG. 3E and FIG. 12) indicating that the observed activation of CD4+ T-cells was HLA class II-restricted. An EBV antigen-specific CD4+ T-cell clone was tested directed against the FGQ, an epitope from an EBV glycoprotein gp350 (Adhikary, *J. Exp. Med.* 203, 995-1006 (2006)) and observed reduced T-cell activities with target B-cells infected with wt/B95-8 EBV compared with ΔmiR EBVs five days after infection (FIG. 9). T-cell activity against B-cells was barely detected at 15 days post infection when the viral antigen gp350 was no longer present because it is a component of the virus particle and presented immediately after B-cell infection (Adhikary, loc. cit.) but is not synthesized during latency (Kalla et al. *Proc. Natl. Acad. Sci. U.S.A.* 107, 850-855 (2010)).

EBV-specific CD4+ T-cells have cytolytic activity (Adhikary, loc. cit.). In allogeneic HLA-matched conditions, EBV-specific CD4+ T-cells consistently showed stronger cytolysis of target B-cells infected with ΔmiR EBV than cells infected wt/B95-8 EBV (FIG. 3F). EBV miRNAs clearly inhibited the recognition of infected B-cells by HLA class II-restricted CD4+ T-cells early after infection.

It was found also that EBV miRNAs impair recognition of infected B-cells by MHC class I-restricted, EBV-specific CD8+ T-cells in addition to CD4+ T-cells. These tests used co-culture assays with EBV-infected B-cells and polyclonal EBV-specific CD8+ T-cells as well as CD8+ T-cell clones specific for certain EBV antigens. IFN-γ secretion by the CD8+ T-cells was measured upon overnight cultivation with primary B-cells that had been infected with the two different EBV strains 15 days earlier (FIG. 4A). In accordance with their HLA restriction (and only in autologous and matched settings), CD8⁺ T-cells released IFN-γ after co-culture with ΔmiR EBV-infected B-cells but less so when co-cultured with wt/B95-8 EBV-infected B-cells (FIG. 4B and FIG. 12). Similarly, B-cells infected with ΔmiR EBV were significantly killed by EBV-specific CD8⁺ T-cells relative to B-cells infected with wt/B95-8 EBV expressing miRNAs (FIG. 4C). Finally, IFN-γ release of the CD8⁺ T-cell clone specific for the IED epitope of viral protein LMP2 presented by HLA-B*40 (FIG. 10) (Lautscham et al., *J. Exp. Med.* 194, 1053-1068 (2001)) was strongly and consistently reduced when co-cultured with wt/B95-8 EBV-infected B-cells compared with ΔmiR EBV-infected B-cells (FIG. 4D). HLA-B*40 but not LMP2 expression was affected by EBV miRNAs (FIG. 4D and FIG. 11). These results suggest that EBV miRNAs control antigen processing and presentation to protect infected B-cells from the recognition by EBV-specific CD8⁺ T-cells.

Example 8

EBV eventually resides in most people in non-proliferating B-cells largely invisible to a host's immune response (Thorley-Lawson, *J. Allergy Clin. Immunol.* 116, 251-261 (2005)). However, it induces proliferation of the B-cells it initially infects and fosters their survival. It was found that EBV encodes miRNAs that regulate multiple facets of a hosts adaptive immune response in newly infected B-cells. EBV-infected B-cells lacking viral miRNAs are deficient both in affecting these responses and in other miRNA-dependent functions including an inhibition of apoptosis (Seto, loc. cit.). These latter defects have precluded comparisons of B-cells newly infected with wt/B95-8 or ΔmiR in humanized mouse models because of the defects in survival of the latter cells (C. Münz, personal communication). Functional assays in culture show compellingly that EBV's miRNAs inhibit the secretion of cytokines, inhibit antigen processing and presentation, inhibit the differentiation of CD4⁺ T-cells and their recognition of infected B-cells, and inhibit the recognition of those cells by EBV-specific CD8⁺ T-cells. The breadth of EBV's use of its miRNAs to inhibit adaptive and innate immune responses (Nachmani et al. *Cell Host Microbe.* 5, 376-385 (2009)) is unprecedented and would foster its efficient establishment of a life-long infection.

Example 9

VLP production was induced by transfection of producer cells as described in Hettich et al. (Gene Therapy, 2006, vol. 13, pages 844-856). The supernatant was filtered through a 1.2 µm filter and concentrated by ultracentrifugation at 100,000×g for 2 hours. Finally, the pellet was resuspended in 1.5 mL PBS.

A human EBV-immortalized B-cell line (LCL) was plated into a 96-well plate (5*10^4 cells/well) and incubated with VLPs (1*10^4 particles/cell) with miRNAs or lacking all miRNAs (ΔmiRNAs) in a total volume of 200 µl/well. After 24 h of incubation, 100 µl of the culture medium was removed and the cells were washed by adding 100 µl of RPMI without supplements and centrifugation for 5 minutes at 300×g. Again, 100 µl of the medium were removed and LCLs were mixed with an HLA-matched CD4+ T-cell clone (100 µl cell culture medium containing 5*10^4 cells) specific for the EBV tegument protein BNRF1 (ratio LCLs:T cells=1:1) and then co-cultivated for another 24 hours. Activation of T cells was quantified in a IFNγ-ELISA assay according to the manufacturer's protocol (human IFNγ-ELISA development kit (ALP), Mabtech). The assay was performed with 5 technical replicates. Results of the assay are shown in FIG. 13.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. An Epstein-Barr virus like particle (EBVLP) comprising Epstein-Barr virus (EBV) proteins, where in at least one of the three particular EBV miRNAs miR-BART17, miR-BART10, and miR-BART22 is physically absent from said EBVLP and wherein said EBVLP is substantially free of an EBV genome.

2. The EBVLP of claim 1, wherein said EBV miRNA is due to genetic modification to a nucleic acid molecule encoding the EBVLP, wherein the genetic modification effects that said EBV miRNA is not expressed, the precursor of said EBV miRNA has a wrong 3D structure, the precursor of said EBV miRNA is not further processed, said precursor of said EBV miRNA is degraded by the cell, said EBV miRNA coding loci has a scrambled sequence, and/or said EBV miRNA coding loci is deleted.

3. The EBVLP of claim 1, wherein said EBVLP leads to an increased immune response when compared to a EBVLP that comprises said particular EBV miRNA of claim 1, wherein said increase is at least 5% as determined in a quantitative ELISA, comprising measuring the concentration of proinflammatory cytokines in the supernatant of immune cells incubated with the EBVLP of claim 1 and comparing said cytokine concentration to the cytokine concentration in the supernatant of immune cells incubated with EBVLPs comprising miRNA identical to the wild type virus.

4. The EBVLP of claim 1, wherein an at least one nucleic acid molecule encoding said EBV proteins is genetically modified such that it is not packaged in the EBVLPs.

5. The EBVLP of claim 1, wherein at least one nucleic acid molecule encoding said EBV proteins comprises
   (i) at least one gene encoding an EBV protein required for cellular transformation, which is genetically modified such that said EBV protein is non-functional; and/or
   (ii) at least one gene encoding an EBV protein required for inducing virus synthesis, which is genetically modified such that said EBV protein is non-functional.

6. The EBVLP of claim 1, wherein
   (i) an at least one nucleic acid molecule encoding said EBV proteins comprises at least one gene, encoding an EBV protein required for B-cell transformation, selected from the group consisting of EBNA1, EBNA-LP, EBNA2, LMP1, LMP2, EBNA3A, and EBNA3C, which is genetically modified such that the EBV protein is non-functional;
   (ii) an at least one nucleic acid molecule encoding said EBV proteins comprises at least one gene, encoding an EBV protein required for inducing virus synthesis, selected from the group consisting of BZFL1, BRLF1 and BMLF1, which is genetically modified such that the EBV protein is non-functional;
   (iii) an at least one nucleic acid molecule encoding said EBV proteins lacks the packaging element TR;
   (iv) an at least one nucleic acid molecule encoding said EBV proteins comprises at least one gene encoding an EBV protein required for packaging of EBV DNA, selected from the group consisting of BFLF1, BBRF1, BGRF1, BDRF1, BALF3, BFRF1A, and BFRF1, which is genetically modified such that said EBV protein is or non-functional.

7. An engineered nucleic acid molecule comprising a sequence encoding the EBVLP of claim 1.

8. A vector comprising the nucleic acid molecule of claim 7.

9. A composition of matter comprising at least two nucleic acid molecules of claim 7.

10. An isolated host cell transfected with the nucleic acid molecule of claim 7, the vector of claim 8, or the of claim 9.

11. A method for generating an Epstein-Barr VLP (EBVLP), the method comprising:
   (i) culturing the isolated host cell of claim 10 under conditions that allow expression of the EBV proteins; and
   (ii) obtaining said EBVLP.

12. The method of claim 11, comprising after step (i) and prior to step (ii) a further step (i'), comprising inducing the replicative phase of the Epstein-Barr virus, wherein said replicative phase is induced by expressing at least one gene encoding an EBV protein that is required for inducing EBV synthesis, wherein the at least one gene comprised by the at least one nucleic acid molecule encoding the EBV proteins of the EBVLP, has been genetically modified, such that said EBV protein is non-functional, wherein said gene is expressed from a stably transfected vector comprised by said host cell.

13. A vaccine composition comprising the EBVLP of claim 1 further comprising an excipient.

14. The vaccine composition of claim 13, further comprising one or more viral or non-viral polypeptides, one or more viral or non-viral nucleic acid sequences and/or vaccine adjuvants, wherein said one or more viral polypeptides or said one or more viral nucleic acid sequences are not from the same virus as the EBVLP in said vaccine composition.

15. A method of treating or preventing a disease associated with EBV infection in a subject comprising administering
   i) the EBVLP of claim 1,
   ii) the vaccine composition of claim 13, or
   iii) the vaccine composition of claim 13, and further comprising one or more viral or non-viral polypeptides, one or more viral or non-viral nucleic acid sequences and/or vaccine adjuvants, wherein said one or more viral polypeptides or said one or more viral nucleic acid sequences are not from the same virus as the EBVLP in said vaccine composition.

16. A kit comprising
   i) the EBVLP of claim 1,
   ii) the nucleic acid molecule of claim 7,
   iii) the vector of claim 8,
   iv) the composition of claim 9,
   v) an isolated host cell comprising the nucleic acid molecule claim 7,
   vi) a vaccine composition comprising the EBVLP of claim 1, and/or
   vii) a vaccine composition comprising the EBVLP of claim 1 and an excipient, and further comprising one or more viral or non-viral polypeptides, one or more viral or non-viral nucleic acid sequences and/or vaccine adjuvants, wherein said one or more viral polypeptides or said one or more viral nucleic acid sequences are not from the same virus as the EBVLP in said vaccine composition.

17. The method of claim 11, wherein a genetic modification to the nucleic acid molecule, which the isolated host cell is transfected with, encoding the EBVLP effects that EBV miRNA is not expressed, the precursor of said EBV miRNA has a wrong 3D structure, the precursor of said EBV miRNA is not further processed, the precursor of said EBV miRNA is degraded by the cell, EBV miRNA coding loci has a scrambled sequence, and/or EBV miRNA coding loci is deleted.

18. The EBVLP of claim 4, wherein
   (i) the at least one nucleic acid molecule encoding said EBV proteins lacks a functional cis-acting element required for packaging; or
   (ii) the at least one nucleic acid molecule encoding said EBV proteins comprises at least one gene encoding an EBV protein required for packaging, which is genetically modified such that said EBV protein is not expressed or non-functional.

19. The method of claim 12, wherein
   (a) expression of said gene is inducibly regulated, and/or
   (b) said gene encoding said EBV protein is selected from the group consisting of BZLF1, BRLF1 and BMLF1.

* * * * *

SEQUENCE LISTING

```
Sequence total quantity: 24
SEQ ID NO: 1           moltype = RNA  length = 22
FEATURE                Location/Qualifiers
misc_feature           1..22
                       note = Epstein-Barr virus BART2 miRNA
source                 1..22
                       mol_type = other RNA
                       organism = synthetic construct
SEQUENCE: 1
tattttctgc attcgccctt gc                                           22

SEQ ID NO: 2           moltype = RNA  length = 53
FEATURE                Location/Qualifiers
misc_feature           1..53
                       note = Predicted IL12B targetsequence of BART2 1
source                 1..53
                       mol_type = other RNA
                       organism = synthetic construct
SEQUENCE: 2
ggcaggtggc ttcttaacag ccctgtgaga agcagacaga tgcaaagaaa atc        53

SEQ ID NO: 3           moltype = RNA  length = 53
FEATURE                Location/Qualifiers
misc_feature           1..53
                       note = mutated IL12B targetsequence of BART2 1
source                 1..53
                       mol_type = other RNA
                       organism = synthetic construct
SEQUENCE: 3
ggcaggtggc ttcttaacag ccctgtgaga agcagacaga tgcaaagttt ttc        53

SEQ ID NO: 4           moltype = RNA  length = 41
FEATURE                Location/Qualifiers
misc_feature           1..41
                       note = Predicted IL12B targetsequence of BART2 2
source                 1..41
                       mol_type = other RNA
                       organism = synthetic construct
SEQUENCE: 4
agcatgtttg aacctgatac acaattatga ccagaaaata t                      41

SEQ ID NO: 5           moltype = RNA  length = 41
FEATURE                Location/Qualifiers
misc_feature           1..41
                       note = mutated IL12B targetsequence of BART2 2
source                 1..41
                       mol_type = other RNA
                       organism = synthetic construct
SEQUENCE: 5
agcatgtttg aacctgatac acaattatga ccagttttta t                      41

SEQ ID NO: 6           moltype = RNA  length = 23
FEATURE                Location/Qualifiers
misc_feature           1..23
                       note = Epstein-Barr virus BART10 miRNA
source                 1..23
                       mol_type = other RNA
                       organism = synthetic construct
```

-continued

```
SEQUENCE: 6
tacataacca tggagttggc tgt                                               23

SEQ ID NO: 7            moltype = RNA   length = 17
FEATURE                 Location/Qualifiers
misc_feature            1..17
                        note = Predicted IL12B targetsequence of BART10 1
source                  1..17
                        mol_type = other RNA
                        organism = synthetic construct
SEQUENCE: 7
tcagctaatt tatgtat                                                      17

SEQ ID NO: 8            moltype = RNA   length = 17
FEATURE                 Location/Qualifiers
misc_feature            1..17
                        note = mutated IL12B targetsequence of BART10 1
source                  1..17
                        mol_type = other RNA
                        organism = synthetic construct
SEQUENCE: 8
tcagctaatt ttacaat                                                      17

SEQ ID NO: 9            moltype = RNA   length = 40
FEATURE                 Location/Qualifiers
misc_feature            1..40
                        note = Predicted IL12B targetsequence of BART10 2
source                  1..40
                        mol_type = other RNA
                        organism = synthetic construct
SEQUENCE: 9
gggccttcat gctatttaaa tatttaagta atttatgtat                             40

SEQ ID NO: 10           moltype = RNA   length = 40
FEATURE                 Location/Qualifiers
misc_feature            1..40
                        note = mutated IL12B targetsequence of BART10 2
source                  1..40
                        mol_type = other RNA
                        organism = synthetic construct
SEQUENCE: 10
gggccttcat gctatttaaa tatttaagta attttacaat                             40

SEQ ID NO: 11           moltype = RNA   length = 23
FEATURE                 Location/Qualifiers
misc_feature            1..23
                        note = Epstein-Barr virus BART22 miRNA
source                  1..23
                        mol_type = other RNA
                        organism = synthetic construct
SEQUENCE: 11
ttacaaagtc atggtctagt agt                                               23

SEQ ID NO: 12           moltype = RNA   length = 31
FEATURE                 Location/Qualifiers
misc_feature            1..31
                        note = Predicted IL12B targetsequence of BART22
source                  1..31
                        mol_type = other RNA
                        organism = synthetic construct
SEQUENCE: 12
ggctgaacta ataaaaactc ttctttgtaa t                                      31

SEQ ID NO: 13           moltype = RNA   length = 31
FEATURE                 Location/Qualifiers
misc_feature            1..31
                        note = mutated IL12B targetsequence of BART22
source                  1..31
                        mol_type = other RNA
                        organism = synthetic construct
SEQUENCE: 13
ggctgaacta ataaaaactc ttctaacaaa t                                      31

SEQ ID NO: 14           moltype = RNA   length = 22
FEATURE                 Location/Qualifiers
misc_feature            1..22
                        note = Epstein-Barr virus BHRF1-3 miRNA
source                  1..22
                        mol_type = other RNA
```

```
                                organism = synthetic construct
SEQUENCE: 14
taacgggaag tgtgtaagca ca                                            22

SEQ ID NO: 15           moltype = RNA  length = 10
FEATURE                 Location/Qualifiers
misc_feature            1..10
                        note = Predicted TAP2 targetsequence of BHRF1-3
source                  1..10
                        mol_type = other RNA
                        organism = synthetic construct
SEQUENCE: 15
gtcccgttgt                                                          10

SEQ ID NO: 16           moltype = RNA  length = 10
FEATURE                 Location/Qualifiers
misc_feature            1..10
                        note = mutated TAP2 targetsequence of BHRF1-3
source                  1..10
                        mol_type = other RNA
                        organism = synthetic construct
SEQUENCE: 16
gtccgcaagt                                                          10

SEQ ID NO: 17           moltype = RNA  length = 22
FEATURE                 Location/Qualifiers
misc_feature            1..22
                        note = Epstein-Barr virus BART1 miRNA
source                  1..22
                        mol_type = other RNA
                        organism = synthetic construct
SEQUENCE: 17
tagcaccgct atccactatg tc                                            22

SEQ ID NO: 18           moltype = RNA  length = 24
FEATURE                 Location/Qualifiers
misc_feature            1..24
                        note = Predicted IL12B targetsequence of BART1
source                  1..24
                        mol_type = other RNA
                        organism = synthetic construct
SEQUENCE: 18
aatatggctc catgaaggtg ctac                                          24

SEQ ID NO: 19           moltype = RNA  length = 24
FEATURE                 Location/Qualifiers
misc_feature            1..24
                        note = mutated IL12B targetsequence of BART1
source                  1..24
                        mol_type = other RNA
                        organism = synthetic construct
SEQUENCE: 19
aatatggctc catgaagcac gtac                                          24

SEQ ID NO: 20           moltype = RNA  length = 22
FEATURE                 Location/Qualifiers
misc_feature            1..22
                        note = Epstein-Barr virus BART17 miRNA
source                  1..22
                        mol_type = other RNA
                        organism = synthetic construct
SEQUENCE: 20
taagaggacg caggcataca ag                                            22

SEQ ID NO: 21           moltype = RNA  length = 20
FEATURE                 Location/Qualifiers
misc_feature            1..20
                        note = Predicted TAP2 targetsequence of BART17
source                  1..20
                        mol_type = other RNA
                        organism = synthetic construct
SEQUENCE: 21
ggtttgctaa ttcctcttgc                                               20

SEQ ID NO: 22           moltype = RNA  length = 20
FEATURE                 Location/Qualifiers
misc_feature            1..20
                        note = mutated TAP2 targetsequence of BART17 1
source                  1..20
```

```
                       mol_type = other RNA
                       organism = synthetic construct
SEQUENCE: 22
ggtttgctaa ttcgagatgc                                                    20

SEQ ID NO: 23          moltype = RNA  length = 16
FEATURE                Location/Qualifiers
misc_feature           1..16
                       note = Predicted TAP2 targetsequence of BART17 2
source                 1..16
                       mol_type = other RNA
                       organism = synthetic construct
SEQUENCE: 23
tcctactatc ctcttt                                                        16

SEQ ID NO: 24          moltype = RNA  length = 16
FEATURE                Location/Qualifiers
misc_feature           1..16
                       note = mutated TAP2 targetsequence of BART17 2
source                 1..16
                       mol_type = other RNA
                       organism = synthetic construct
SEQUENCE: 24
tcctactatc gagatt                                                        16
```